(12) United States Patent
Dumas

(10) Patent No.: US 10,155,718 B2
(45) Date of Patent: Dec. 18, 2018

(54) PROCESS TO PREPARE 3-METHYL-2-NITROBENZOIC ACID BY AIR OXIDATION

(71) Applicant: FMC CORPORATION, Philadelphia, PA (US)

(72) Inventor: Donald J. Dumas, Wilmington, DE (US)

(73) Assignee: FMC CORPORATION, Philadelphia, PA (US)

( * ) Notice: Subject to any disclaimer, the term of this patent is extended or adjusted under 35 U.S.C. 154(b) by 0 days.

(21) Appl. No.: 15/819,646

(22) Filed: Nov. 21, 2017

(65) Prior Publication Data

US 2018/0072653 A1  Mar. 15, 2018

Related U.S. Application Data

(62) Division of application No. 15/313,365, filed as application No. PCT/US2015/033131 on May 29, 2015, now Pat. No. 9,828,328.

(60) Provisional application No. 62/004,459, filed on May 29, 2014, provisional application No. 62/027,275, filed on Jul. 22, 2014.

(51) Int. Cl.
*C07C 201/12* (2006.01)
*C07C 253/14* (2006.01)
*C07C 231/02* (2006.01)

(52) U.S. Cl.
CPC .......... *C07C 201/12* (2013.01); *C07C 231/02* (2013.01); *C07C 253/14* (2013.01)

(58) Field of Classification Search
CPC .............................. C07C 201/12; C07C 231/02
See application file for complete search history.

(56) References Cited

U.S. PATENT DOCUMENTS

| | | | |
|---|---|---|---|
| 4,329,518 A | 5/1982 | Plummer | |
| 5,591,890 A | 1/1997 | Jacobson | |
| 8,242,279 B2 * | 8/2012 | Dumas | C07C 253/14 546/275.4 |
| 8,247,570 B2 * | 8/2012 | Dumas | C07C 253/14 546/276.1 |
| 8,871,939 B2 * | 10/2014 | Kristjansdottir | C07C 231/10 546/163 |
| 9,828,328 B2 * | 11/2017 | Jacobson | C07C 201/12 |

FOREIGN PATENT DOCUMENTS

| | | |
|---|---|---|
| CN | 103396467 | 11/2013 |
| JP | 5-132450 A | 5/1993 |
| JP | 2001-11026 A | 1/2001 |
| JP | 2006-232814 A | 1/2006 |
| JP | 2009-062277 A | 3/2009 |
| WO | 2004-014873 | 2/2004 |

OTHER PUBLICATIONS

Jacobson et al., "New Air Oxidation Route to Ortho-Nitroaromatic Acids", Chemical Industries, 68, 87-96, Oct. 1, 1996.
Noelting et al., (1906), "On the vic. Amino-iso-phtalic acid", Mulhouse i/E. Chemistry School, 39: 73-76. doi. 10. 1002/cber. 19060390115.
PCT Search Report for WO2015/184229 dated Aug. 6, 2015.

* cited by examiner

*Primary Examiner* — Golam M Shameem
(74) *Attorney, Agent, or Firm* — Linda D. Birch

(57) ABSTRACT

A method for preparing 3-methyl-2-nitrobenzoic acid is disclosed wherein 1,3-dimethyl-2-nitrobenzene is combined with an oxidation catalyst in the presence of an oxygen source and an initiator, provided that less than 99% of the 1,3-dimethyl-2-nitrobenzene is oxidized.
A method for preparing compounds of Formula 7 and Formula 11 is also disclosed wherein the method is characterized by using 3-methyl-2-nitrobenzoic acid as prepared by the method disclosed above

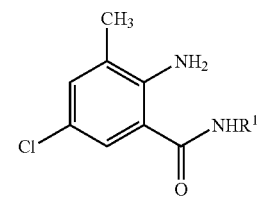

7

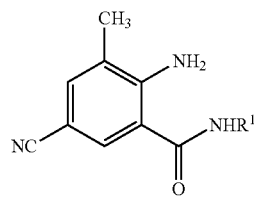

11 wherein $R^1$ is $C_1$-$C_7$ alkyl, $C_3$-$C_6$ cycloalkyl or $C_4$-$C_7$ alkylcycloalkyl.

15 Claims, No Drawings

PROCESS TO PREPARE 3-METHYL-2-NITROBENZOIC ACID BY AIR OXIDATION

BACKGROUND OF THE INVENTION

A need exists for additional methods to prepare 3-methyl-2-nitrobenzoic acid that are selective and cost-effiective. 3-Methyl-2-nitrobenzoic acid is useful as in intermediate in the preparation of agrochemicals such as Rynaxypyr® and Cyazypyr®.

Oxidation of mono-alkyl ortho-nitroalkylaromatic compounds is exemplified in Jacobsen, U.S. Pat. No. 5,591,890. Selective oxidation of one alkyl group in ortho-nitroalkylaromatic compounds with two or more alkyl groups is not disclosed in this patent.

Oxidation of 2-nitro-p-xylene is disclosed in Jacobson and Ely, *Chemical Industries* 1996, 68, 87-96. Selective oxidation of one alkyl group in ortho-nitroalkylaromatic compounds with two or more alkyl groups is not disclosed in this publication.

Oxidation of 2-nitro-m-xylene is disclosed in JP05132450 using $H_2SO_4$ and stoichiometric $CrO_3$.

SUMMARY OF THE INVENTION

This invention provides a method for preparing a compound of Formula 2

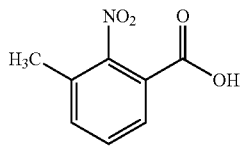

2 comprising, contacting a compound of Formula 1

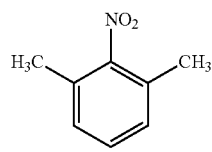

1 with an oxidation catalyst in the presence of an oxygen source and an initiator provided that less than 99% of a compound of Formula 1 is oxidized.

This invention also provides a method for preparing a compound of Formula 7

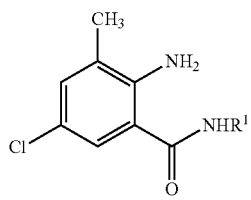

7 wherein $R^1$ is $C_1$-$C_7$ alkyl, $C_3$-$C_6$ cycloalkyl or $C_4$-$C_7$ alkylcycloalkyl; the method characterized by using a compound of Formula 2 as prepared by the method disclosed above.

This invention also provides a method for preparing a compound of Formula 11

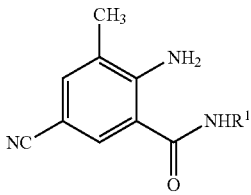

11 wherein $R^1$ is $C_1$-$C_7$ alkyl, $C_3$-$C_6$ cycloalkyl or $C_4$-$C_7$ alkylcycloalkyl; the method characterized by using compound of Formula 2 as prepared by the method disclosed above.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method, article, or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of". Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, the compound of Formula 1 is 1,3-dimethyl-2-nitrobenzene and the compound of Formula 2 is 3-methyl-2-nitrobenzoic acid.

As referred to in the present disclosure and claims, the term "alkyl", used either alone or in compound words such as "alkylcycloalkyl" includes straight-chain or branched alkyl, such as, methyl, ethyl, n-propyl, i-propyl, or the different butyl, pentyl or hexyl isomers. The term "cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The total number of carbon atoms in a substituent group is indicated by the "$C_i$-$C_j$" prefix where i and j are numbers from 1 to 7. For example, $C_4$-$C_7$ alkylcycloalkyl designates methylcyclopropyl (i.e. $C_4$ alkylcycloalkyl) through butylcyclopropyl or methylcyclohexyl (i.e. $C_7$ alkylcycloalkyl).

As used herein, the term "combining" refers to the act of "mixing", "intermixing" or "putting together" for the purposes of bringing two or more chemical compounds in close contact so as to promote a chemical reaction. For example certain substrates, reagents or ingredients, reagents as described in the Summary of the Invention are "combined" with each other in an appropriate vessel, container or apparatus in such a fashion that the substrates, reagents or ingredients can chemically react with one another so that a new product can be formed.

As used herein the term "selectively oxidizing" means converting only one of two "$CH_3$" moieties appended to the compound of Formula 1 to a "$CO_2H$" moiety (i.e. selectively converting a compound of Formula 1 to a compound of Formula 2). The statement "less than 99% of a compound of Formula 1 is oxidized" means that at least 1% of the compound of Formula 1 is recovered unreacted. As used herein, the term "conversion" is defined as the percent of the compound of Formula 1 that has reacted. The statement "less than 99% of a compound of Formula 1 is oxidized" means that there is less than 99% conversion of the compound of Formula 1 (to oxidation products). As used herein, the term "selectivity" is defined as the number of moles of the compound of Formula 2 produced divided by the number of moles of the compound of Formula 1 reacted (i.e. [moles (2)/moles (1)]×100). As used herein, the term "yield" refers to the mole percentage of product (i.e. the compound of Formula 2) recovered based on the quantity of starting material (i.e. the compound of Formula 1) employed.

As used herein, the term "pressurizing" refers to the act of placing a mixture of ingredients under pressure. Pressurizing is typically accomplished by introducing a compressed gas into a vessel, container or apparatus containing single or multiple substrate(s), reagent(s) or ingredient(s). As described in any of the Embodiments described herein, the pressurizing is performed by adding a gas to the reaction mixture contained in a partially closed system comprising a vessel, container or apparatus. The opening of said vessel, container or apparatus consists of a barrier to allow the escape of the gas at a known pressure. The pressurizing is normally performed with nitrogen or the "oxygen source" which comprises air, a carrier gas enriched with air, a carrier gas enriched with oxygen gas, or oxygen gas alone. For reasons of safety it is preferable to first pressurize the vessel with nitrogen, then heat the vessel to at or near the target operating temperature, and then switch from nitrogen to the oxygen source.

As used herein, the terms "run", "pass" or "batch" refer to a subsequent experiment conducted after an initial experiment wherein some of the components (compound of Formula 1, oxidation catalyst or solvent) are recycled or originate from the initial experiment.

The units of pressure used in this disclosure can be converted for comparison to units of pressure used in other publications. For example, 500 p.s.i.g. equals 34.0 atm or 34.5 bar or 3450 kPa or 3,450,000 newtons/meter$^2$ (N/m$^2$). The abbreviation p.s.i.g. is pounds per square inch as measured on a guage (used in an experimental apparatus) (1 p.s.i.g. equals $6.8948 \times 10^3$ Pascals). Pressure can be measured in atmospheres (atm), bar (defined as approximately atmospheric pressure or 100,000 Pa), Pascals (unit of force per unit area or 1 newton per square meter) or kilo Pascals (kPa defined as the number of Pascals divided by 1000). Of further note the abbreviation 3.45e+006 used in this disclosure means $3.45 \times 10^6$ or 3,450,000.

Embodiments of the present invention include:

Embodiment 1. A method for preparing the compound of Formula 2 comprising,
contacting a compound of Formula 1 with an oxidation catalyst in the presence of an oxygen source and an initiator provided that less than 99 mole % of a compound of Formula 1 is oxidized.

Embodiment 1a. The method of Embodiment 1 wherein the compound of Formula 1, the oxidation catalyst, the oxygen source and the initiator are contacted to form a mixture.

Embodiment 2. The method of Embodiments 1 or 1a wherein the oxidation catalyst (metal catalyst) comprises cobalt(II), cobalt(III), manganese(II), manganese(III), iron (II) or iron(III) salts, or mixtures thereof.

Embodiment 3. The method of Embodiment 2 wherein the oxidation catalyst comprises cobalt(II) or cobalt(III) salts, or mixtures thereof.

Embodiment 4. The method of Embodiment 3 wherein the oxidation catalyst comprises cobalt(II) acetate or cobalt(II) carbonate.

Embodiment 5. The method of Embodiments 3 or 4 wherein the oxidation catalyst comprises cobalt(II) acetate tetrahydrate.

Embodiment 6. The method of any one of Embodiments 1 through 5 wherein the weight percent of the oxidation catalyst (metal catalyst) to the compound of Formula 1 is from about 0.01% to about 20%.

Embodiment 7. The method of Embodiment 6 wherein the weight percent of the oxidation catalyst to the compound of Formula 1 is from about 0.1% to about 10%.

Embodiment 8. The method of Embodiment 7 wherein the weight percent of the oxidation catalyst to the compound of Formula 1 is from about 0.5% to about 7%.

Embodiment 9. The method of Embodiment 8 wherein the weight percent of the oxidation catalyst to the compound of Formula 1 is from about 0.75% to about 5%.

Embodiment 10. The method of Embodiment 9 wherein the weight percent of the oxidation catalyst to the compound of Formula 1 is from about 1% to about 3%.

Embodiment 11. The method of Embodiment 10 wherein the weight percent of the oxidation catalyst to the compound of Formula 1 is about 2%.

Embodiment 12. The method of any one of Embodiments 1 through 11 wherein the oxygen source comprises air, a carrier gas enriched with oxygen gas, or oxygen gas.

Embodiment 12a. The method of any one of Embodiments 1 through 11 wherein the oxygen source comprises air, a carrier gas enriched with air, a carrier gas enriched with oxygen gas, or oxygen gas.

Embodiment 13. The method of Embodiment 12 wherein the oxygen source comprises air or a carrier gas enriched with oxygen gas.

Embodiment 13a. The method of Embodiment 12a wherein the oxygen source comprises air or a carrier gas enriched with air.

Embodiment 14. The method of Embodiment 13 wherein the oxygen source comprises air.

Embodiment 14a. The method of Embodiment 13a wherein the oxygen source comprises air.

Embodiment 15. The method of any one of Embodiments 1 through 14a wherein the initiator comprises acetaldehyde, propionaldehyde, metaldehyde, paraldehyde or methylethylketone, or mixtures thereof.

Embodiment 16. The method of Embodiment 15 wherein the initiator comprises acetaldehyde, propionaldehyde or paraldehyde, or mixtures thereof.

Embodiment 17. The method of Embodiment 16 wherein the initiator comprises acetaldehyde.

Embodiment 18. The method of any one of Embodiments 1 through 17 wherein the compound of Formula 1, the oxidation catalyst, the oxygen source and the initiator are contacted in the presence of a suitable solvent.

Embodiment 19. The method of Embodiment 18 wherein the suitable solvent comprises acetic acid, propionic acid, butyric acid, valeric acid, hexanoic acid, 2-ethylhexanoic acid, acetic anhydride, o-dichlorobenzene or chlorobenzene, or mixtures thereof.

Embodiment 20. The method of Embodiment 19 wherein the suitable solvent comprises acetic acid, propionic acid, hexanoic acid or 2-ethylhexanoic acid, or mixtures thereof.

Embodiment 21. The method of Embodiment 20 wherein the suitable solvent comprises acetic acid.

Embodiment 22. The method of any one of Embodiments 18 through 21 wherein the suitable solvent further comprises water.

Embodiment 23. The method of Embodiment 22 wherein the suitable solvent comprises acetic acid or a mixture of acetic acid and water.

Embodiment 24. The method of Embodiment 23 wherein the suitable solvent comprises a mixture of acetic acid and water.

Embodiment 25. The method of Embodiment 24 wherein the suitable solvent comprises a mixture of less than 10 wt % water in acetic acid.

Embodiment 26. The method of Embodiment 25 wherein the suitable solvent comprises a mixture of less than 5 wt % water in acetic acid.

Embodiment 27. The method of Embodiment 26 wherein the suitable solvent comprises a mixture of less than 1 wt % water in acetic acid.

Embodiment 28. The method of any one of Embodiments 1 through 27 wherein the weight % of the compound of Formula 1 in the suitable solvent is from about 4% to about 90%.

Embodiment 28a. The method of Embodiment 28 wherein the weight % of the compound of Formula 1 in the suitable solvent is from about 4% to about 80%.

Embodiment 28b. The method of Embodiment 28 wherein the weight % of the compound of Formula 1 in the suitable solvent is from about 4% to about 70%.

Embodiment 29. The method of Embodiment 28a wherein the weight % of the compound of Formula 1 in the suitable solvent is from about 20% to about 75%.

Embodiment 29a. The method of Embodiment 28b wherein the weight % of the compound of Formula 1 in the suitable solvent is from about 20% to about 60%.

Embodiment 30. The method of Embodiment 29 wherein the weight % of the compound of Formula 1 in the suitable solvent is from about 40% to about 70%.

Embodiment 30a. The method of Embodiment 29a wherein the weight % of the compound of Formula 1 in the suitable solvent is from about 30% to about 50%.

Embodiment 31. The method of Embodiment 30 wherein the weight % of the compound of Formula 1 in the suitable solvent is about 67%.

Embodiment 31a. The method of Embodiment 30a wherein the weight % of the compound of Formula 1 in the suitable solvent is about 50%.

Embodiment 32. The method of any one of Embodiments 1 through 31a wherein the mixture formed by contacting the compound of Formula 1, the oxidation catalyst, the oxygen source and the initiator is heated to a temperature of about 60° C. to about 150° C.

Embodiment 33. The method of Embodiment 32 wherein the mixture is heated to a temperature of about 80° C. to about 120° C.

Embodiment 34. The method of Embodiment 33 wherein the mixture is heated to a temperature of about 90° C. to about 115° C.

Embodiment 35. The method of Embodiment 34 wherein the mixture is heated to a temperature of about 100° C.

Embodiment 36. The method any one of Embodiments 1 through 35 wherein the mixture formed by contacting the compound of Formula 1, the oxidation catalyst, the oxygen source and the initiator is pressurized from about 1400 kPa (about 200 p.s.i.g or $0.345e+006$ newtons/meter$^2$) to about 6900 kPa (about 1000 p.s.i.g or $6.89e+006$ newtons/meter$^2$).

Embodiment 37. The method of Embodiment 36 wherein the mixture is pressurized from about 1700 kPa (about 250 p.s.i.g. or $1.72e+006$ newtons/meter$^2$) to about 5200 kPa (about 750 p.s.i.g or $5.17e+006$ newtons/meter$^2$).

Embodiment 38. The method of Embodiment 37 wherein the mixture is pressurized from about 2100 kPa (about 300 p.s.i.g. or $2.07e+006$ newtons/meter$^2$) to about 4800 kPa (about 700 p.s.i.g or $4.83e+006$ newtons/meter$^2$).

Embodiment 39. The method of Embodiment 38 wherein the mixture is pressurized from about 2800 kPa (about 400 p.s.i.g.or $2.76e+006$ newtons/meter$^2$) to about 4100 kPa (about 600 p.s.i.g or $4.14e+006$ newtons/meter$^2$).

Embodiment 40. The method of Embodiment 39 wherein the mixture is pressurized to about 3500 kPa (about 500 p.s.i.g or $3.45e+006$ newtons/meter$^2$).

Embodiment 41. The method of any one of Embodiments 1 through 40 wherein less than about 90% of a compound of Formula 1 is oxidized (less than about 90% of a compound of Formula 1 is converted).

Embodiment 42. The method of Embodiment 41 wherein less than about 80% of a compound of Formula 1 is oxidized (less than about 80% of a compound of Formula 1 is converted).

Embodiment 43. The method of Embodiment 42 wherein less than 70% of a compound of Formula 1 is oxidized (less than about 70% of a compound of Formula 1 is converted).

Embodiment 44. The method of Embodiment 43 wherein less than 60% of a compound of Formula 1 is oxidized (less than about 60% of a compound of Formula 1 is converted).

Embodiment 45. The method of Embodiment 44 wherein less than 50% of a compound of Formula 1 is oxidized (less than about 50% of a compound of Formula 1 is converted).

Embodiment 46. The method of Embodiment 45 wherein less than 40% of a compound of Formula 1 is oxidized (less than about 40% of a compound of Formula 1 is converted).

Embodiment 47. The method of Embodiment 46 wherein less than 30% of a compound of Formula 1 is oxidized (less than about 30% of a compound of Formula 1 is converted).

Embodiment 48. The method of Embodiment 47 wherein less than 20% of a compound of Formula 1 is oxidized (less than about 20% of a compound of Formula 1 is converted).

Embodiment 49. The method of any one of Embodiments 1 through 48 wherein the selectivity is greater than 40%.

Embodiment 50. The method of Embodiment 49 wherein the selectivity is greater than 50%.

Embodiment 51. The method of Embodiment 50 wherein the selectivity is greater than 60%.

Embodiment 52. The method of Embodiment 51 wherein the selectivity is greater than 70%.

Embodiment 53. The method of Embodiment 52 wherein the selectivity is greater than 80%.

Embodiment 54. The method of Embodiment 53 wherein the selectivity is greater than 90%.

Embodiment 55. The method of any one of Embodiments 1 through 54 further comprising isolating the compound of Formula 2 by filtering and optionally washing with a wash solvent.

Embodiment 56. The method of any one of Embodiments 1 through 55 wherein the wash solvent comprises at least one solvent selected from acetic acid, propionic acid, butyric acid, valeric acid, hexanoic acid, acetic anhydride, o-dichlorobenzene and chlorobenzene, and mixtures thereof.

Embodiment 57. The method of Embodiment 56 wherein the wash solvent further comprises water.

Embodiment 58. The method of Embodiments 56 and 57 wherein the wash solvent comprises acetic acid or a mixture of acetic acid and water.

Embodiment 59. The method of any one of Embodiments 1 through 58 further comprising isolating the compound of Formula 2 by filtering and purifying the isolated compound of Formula 2 by recrystallizing from a recrystallization solvent.

Embodiment 60. The method of any one of Embodiments 1 through 59 wherein the recrystallization solvent comprises acetic acid or a mixture of acetic acid and water or a mixture of acetic acid, water and an alkali metal hydroxide.

Embodiment 61. The method of any one of Embodiments 1 through 58 further comprising isolating the compound of Formula 2 by filtering and purifying the isolated compound of Formula 2 by dissolving in aqueous base followed by precipitating by adding aqueous acid.

Embodiment 62. The method of Embodiment 61 wherein the aqueous base is aqueous sodium hydroxide and the aqueous acid is aqueous hydrochloric acid.

Embodiment 63. The method of any one of Embodiments 1 through 58 wherein the isolating the compound of Formula 2 by filtering further comprises recycling the filtrate directly in a subsequent oxidation run after combination with additional 1,3-dimethyl-2-nitrobenzene (1) and optional additional oxidation catalyst and solvent.

Embodiment 63a. The method of any one of Embodiments 1 through 54 further comprising isolating the compound of Formula 2 by filtering and recycling the filtrate directly in a subsequent oxidation run after combination with additional 1,3-dimethyl-2-nitrobenzene (1) and optional additional oxidation catalyst and solvent.

Embodiment D0. The method described in the Summary of the Invention for preparing a compound of Formula 7 using a compound of Formula 2 prepared from a compound of Formula 1.

Embodiment D1. The method of Embodiment D0 for preparing a compound of Formula 7

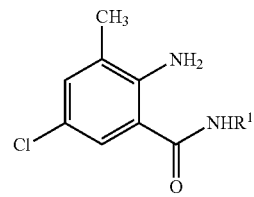

wherein $R^1$ is $C_1$-$C_7$ alkyl, $C_3$-$C_6$ cycloalkyl or $C_4$-$C_7$ alkylcycloalkyl;

comprising (A) contacting a compound of Formula 2

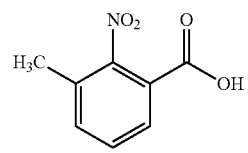

with a reducing agent to form a compound of Formula 3

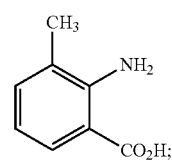

(B) contacting the compound of Formula 3 with $R^2OC(\!=\!O)Cl$ to form a compound of Formula 4

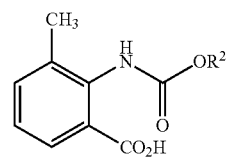

wherein $R^2$ is $C_1$-$C_6$ alkyl or $C_3$-$C_6$ alkenyl, each optionally substituted with up to 3 halogen and up to 1 phenyl;

(C) contacting the compound of Formula 4 with a chlorinating agent to form a compound of Formula 5

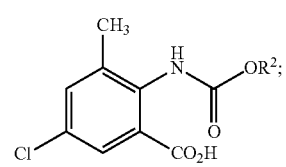

(D) contacting the compound of Formula 5
with a cyclizing agent to form a compound of Formula 6

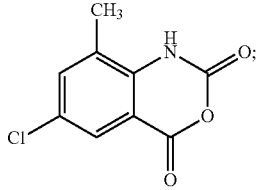

(E) contacting the compound of Formula 6
with $R^1NH_2$ to form the compound of Formula 7;

characterized by using the compound of Formula 2 as prepared by the method described in any of Embodiments 1 through 63a.

Embodiment D2. The method of Embodiment D1 wherein $R^1$ is $C_1$-$C_4$ alkyl or $C_3$-$C_6$ cycloalkyl.

Embodiment D3. The method of Embodiment D2 wherein $R^1$ is methyl, isopropyl, cyclopropyl or t-butyl.

Embodiment D4. The method of Embodiment D3 wherein $R^1$ is methyl or t-butyl.

Embodiment D5. The method of Embodiment D4 wherein $R^1$ is methyl.

Embodiment D6. The method of Embodiment D4 wherein $R^1$ is t-butyl.

Embodiment D7. The method of any one of Embodiments D1 through D6 wherein $R^2$ is $C_1$-$C_4$ alkyl.

Embodiment D8. The method of Embodiment D7 wherein $R^2$ is methyl or ethyl.

Embodiment D9. The method of Embodiment D8 wherein $R^2$ is ethyl.

Embodiment D10. The method of any one of Embodiments D1 through D9 wherein the cyclizing agent is $PBr_3$.

Embodiment D11. The method of any one of Embodiments D1 through D10 wherein the chlorinating agent is HCl and $H_2O_2$.

Embodiment E0. The method described in the Summary of the Invention for preparing a compound of Formula 11 using a compound of Formula 2 prepared from a compound of Formula 1.

Embodiment E1. The method of Embodiment E0 for preparing a compound of Formula 11

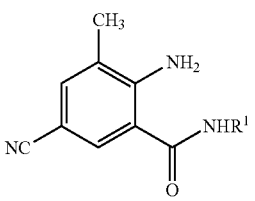

wherein $R^1$ is $C_1$-$C_7$ alkyl, $C_3$-$C_6$ cycloalkyl or $C_4$-$C_7$ alkylcycloalkyl;

comprising (A) contacting a compound of Formula 2

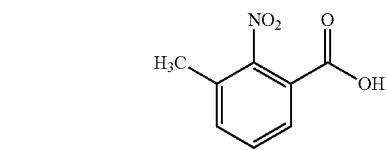

with an activating agent and $R^1NH_2$ to form a compound of Formula 8;

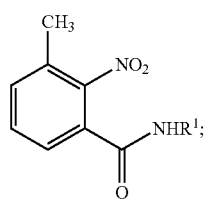

(B) contacting the compound of Formula 8
with a reducing agent to form a compound of Formula 9

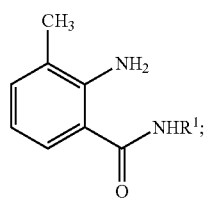

(C) contacting the compound of Formula 9
with a brominating agent to form a compound of Formula 10

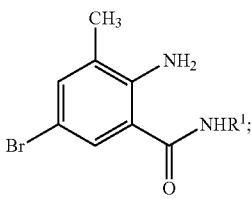

(D) contacting the compound of Formula 10
with a cyanating agent to form the compound of Formula 11;

characterized by using the compound of Formula 2 as prepared by the method described in any of Embodiments 1 through 63a.

Embodiment E2. The method of Embodiment E1 wherein $R^1$ is $C_1$-$C_4$ alkyl or $C_3$-$C_6$ cycloalkyl.

Embodiment E3. The method of Embodiment E2 wherein $R^1$ is methyl, isopropyl, cyclopropyl or t-butyl.

Embodiment E4. The method of Embodiment E3 wherein $R^1$ is methyl or t-butyl.

Embodiment E5. The method of Embodiment E4 wherein $R^1$ is methyl.

Embodiment E6. The method of Embodiment E4 wherein $R^1$ is t-butyl.

Any of the above Embodiments 1 through 63a, D0 through D11 or E0 through E6 of this invention can be combined in any manner.

Additional Embodiments of note include:

Embodiment A1. A method for preparing 3-methyl-2-nitrobenzoic acid (2) comprising the steps of, (i) combining 1,3-dimethyl-2-nitrobenzene (1) with a metal catalyst; (ii) heating the resulting mixture under pressure in the presence of an oxygen source and an initiator; and (iii) oxidizing less than 99 mol% of 1,3-dimethyl-2-nitrobenzene (1).

Embodiment A2. The method of Embodiment A1 wherein 1,3-dimethyl-2-nitrobenzene (1) in step i) is optionally dissolved in a solvent.

Embodiment A3. The method of Embodiment A2 wherein 1,3-dimethyl-2-nitrobenzene (1) is dissolved in a solvent.

Embodiment A4. The method of Embodiment A3 wherein the solvent is selected from a non-oxidizeable solvent, and a mixture thereof.

Embodiment A5. The method of Embodiment A4 wherein the solvent is selected from acetic acid, propionic acid, butyric acid, valeric acid, hexanoic acid, acetic anhydride, o-dichlorobenzene and chlorobenzene, and a mixture thereof.

Embodiment A6. The method of Embodiment A5 wherein the solvent is selected from acetic acid, propionic acid and hexanoic acid, and a mixture thereof.

Embodiment A7. The method of Embodiment A6 wherein the solvent is acetic acid.

Embodiment A8. The method of any one of Embodiments A3 through A6 wherein the solvent is selected from acetic acid, propionic acid and hexanoic acid, and a mixture thereof with water.

Embodiment A9. The method of any one of Embodiments A3 through A6 wherein the solvent is selected from acetic acid and propionic acid, and a mixture thereof with water.

Embodiment A10. The method of any one of Embodiments A3 through A6 wherein the solvent is a mixture of acetic acid with water.

Embodiment A11. The method of Embodiment A10 wherein the solvent is a mixture of at least 75% acetic acid in water.

Embodiment A12. The method of Embodiment A11 wherein the solvent is a mixture of at least 90% acetic acid in water.

Embodiment A13. The method of Embodiment A12 wherein the solvent is a mixture of at least 95% acetic acid in water.

Embodiment A14. The method of any one of Embodiments A1 through A13 wherein the weight ratio of solvent to 1,3-dimethyl-2-nitrobenzene (1) is from about 100:1 to about 0.05:1.

Embodiment A15. The method of Embodiment A14 wherein the weight ratio of solvent to 1,3-dimethyl-2-nitrobenzene (1) is from about 20:1 to about 0.075:1.

Embodiment A16. The method of Embodiment A15 wherein the weight ratio of solvent to 1,3-dimethyl-2-nitrobenzene (1) is from about 10:1 to about 0.1:1.

Embodiment A17. The method of Embodiment A16 wherein the weight ratio of solvent to 1,3-dimethyl-2-nitrobenzene (1) is from about 10:1 to about 0.25:1.

Embodiment A18. The method of Embodiment A17 wherein the weight ratio of solvent to 1,3-dimethyl-2-nitrobenzene (1) is from about 10:1 to about 0.5:1.

Embodiment A19. The method of Embodiment A18 wherein the weight ratio of solvent to 1,3-dimethyl-2-nitrobenzene (1) is from about 5:1 to about 0.66:1.

Embodiment A19a. The method of Embodiment A18 wherein the weight ratio of solvent to 1,3-dimethyl-2-nitrobenzene (1) is about 0.5:1.

Embodiment A20. The method of any one of Embodiments A1 through A19a wherein the metal catalyst is a cobalt(II), cobalt(III), manganese(II), manganese(III), iron (II) or iron(III) metal catalyst.

Embodiment A21. The method of Embodiment A20 wherein the metal catalyst is a cobalt(II) or cobalt(III) metal catalyst.

Embodiment A22. The method of Embodiment A21 wherein the metal catalyst is cobalt(II) acetate or cobalt(II) carbonate.

Embodiment A23. The method of Embodiment A22 wherein the metal catalyst is cobalt(II) acetate tetrahydrate.

Embodiment A24. The method of any one of Embodiments A1 through A23 wherein the weight percent of metal catalyst to 1,3-dimethyl-2-nitrobenzene (1) is from about 0.01% to about 25%.

Embodiment A25. The method of Embodiment A24 wherein the weight percent of metal catalyst is from about 0.1% to about 15%.

Embodiment A26. The method of Embodiment A25 wherein the weight percent of metal catalyst is from about 0.5% to about 10%.

Embodiment A27. The method of Embodiment A26 wherein the weight percent of metal catalyst is from about 0.75% to about 7%.

Embodiment A28. The method of Embodiment A27 wherein the weight percent of metal catalyst is from about 1% to about 5%.

Embodiment A29. The method of Embodiment A28 wherein the weight percent of metal catalyst is from about 2% to about 4%.

Embodiment A29a. The method of Embodiment A29 wherein the weight percent of metal catalyst is about 2%.

Embodiment A30. The method of any one of Embodiments A1 through A29a wherein the heating is to a temperature of at least about 60° C.

Embodiment A31. The method of Embodiment A30 wherein the heating is to a temperature of at least about 70° C.

Embodiment A32. The method of Embodiment A30 or A31 wherein the heating is to a temperature not greater than about 150° C.

Embodiment A33. The method of Embodiment A30 or A31 wherein the heating is to a temperature not greater than about 120° C.

Embodiment A34. The method of Embodiment A30 or A31 wherein the heating is to a temperature not greater than about 110° C.

Embodiment A35. The method of any one of Embodiments A1 through A34 wherein the heating is to a temperature of about 100° C.

Embodiment A36. The method any one of Embodiments A1 through A35 wherein the pressure is from about 50 p.s.i.g (0.345e+006 newtons/meter$^2$) to about 1000 p.s.i.g (from about 1.38e+006 newtons/meter$^2$ to about 6.89e+006 newtons/meter$^2$).

Embodiment A37. The method of Embodiment A36 wherein the pressure is from about 250 to about 750 p.s.i.g (from about 1.72e+006 newtons/meter$^2$ to about 5.17e+006 newtons/meter$^2$.

Embodiment A38. The method of Embodiment A37 wherein the pressure is from about 300 to about 700 p.s.i.g (from about 2.07e+006 newtons/meter$^2$ to about 4.83e+006 newtons/meter2).

Embodiment A39. The method of Embodiment A38 wherein the pressure is from about 400 to about 600 p.s.i.g (from about 2.76e+006 newtons/meter$^2$ to about 4.14e+006 newtons/meter$^2$).

Embodiment A40. The method of Embodiment A39 wherein the pressure is about 500 p.s.i.g (about 3.45e+006 newtons/meter$^2$).

Embodiment A41. The method of any one of Embodiments A1 through A40 wherein the initiator is acetaldehyde, propionaldehyde, metaldehyde, paraldehyde or methylethylketone.

Embodiment A42. The method of Embodiment A41 wherein the initiator is acetaldehyde, propionaldehyde or paraldehyde.

Embodiment A43. The method of Embodiment A42 wherein the initiator is acetaldehyde.

Embodiment A44. The method of any one of Embodiments A1 through A39 wherein the oxygen source comprises air, a carrier gas enriched with oxygen gas, or oxygen gas.

Embodiment A45. The method of Embodiment A44 wherein the oxygen source comprises air or a carrier gas enriched with oxygen gas.

Embodiment A46. The method of Embodiment A45 wherein the oxygen source comprises air.

Embodiment A47. The method of any one of Embodiments A1 through A46 wherein the oxidizing is less than 95 mol % of 1,3-dimethyl-2-nitrobenzene (1) (i.e. The method of any one of Embodiments A1 through A46 wherein less than 95 mol % of 1,3-dimethyl-2-nitrobenzene (1) is oxidized).

Embodiment A48. The method of Embodiment A47 wherein the oxidizing is less than 90 mol %.

Embodiment A49. The method of Embodiment A48 wherein the oxidizing is less than 80 mol %.

Embodiment A50. The method of Embodiment A49 wherein the oxidizing is less than 70 mol %.

Embodiment A51. The method of Embodiment A50 wherein the oxidizing is less than 60 mol %.

Embodiment A52. The method of Embodiment A51 wherein the oxidizing is less than 50 mol %.

Embodiment A53. The method of Embodiment A52 wherein the oxidizing is less than 45 mol %.

Embodiment A54. The method of Embodiment A53 wherein the oxidizing is less than 40 mol %.

Embodiment A55. The method of Embodiment A54 wherein the oxidizing is less than 35 mol %.

Embodiment A56. The method of Embodiment A55 wherein the oxidizing is less than 30 mol %.

Embodiment A57. The method of any one of Embodiments A1 through A56 wherein the selectivity is greater than 40%.

Embodiment A58. The method of Embodiment A57 wherein the selectivity is greater than 55%.

Embodiment A59. The method of Embodiment A58 wherein the selectivity is greater than 65%.

Embodiment A60. The method of Embodiment A59 wherein the selectivity is greater than 75%.

Embodiment A61. The method of Embodiment A60 wherein the selectivity is greater than 85%.

Embodiment A62. The method of Embodiment A61 wherein the selectivity is greater than 90%.

Embodiment A63. The method of Embodiment A62 wherein the selectivity is greater than 95%.

Embodiment A64. The method of any one of Embodiments A1 through A63 further comprising step iv) isolating 3-methyl-2-nitrobenzoic acid (2) by filtering.

Embodiment A65. The method of any one of Embodiments A1 through A64 further comprising step iv) isolating 3-methyl-2-nitrobenzoic acid (2) by filtering, and optionally washing with a wash solvent.

Embodiment A66. The method of any one of Embodiments A1 through A63 further comprising step iv) isolating 3-methyl-2-nitrobenzoic acid (2) by crystallizing, filtering, and optionally washing with a wash solvent.

Embodiment A67. The method of any one of Embodiments A65 or A66 wherein the wash solvent is selected from a non-oxidizeable solvent, and a mixture thereof.

Embodiment A68. The method of Embodiment A67 wherein the wash solvent is selected from acetic acid, propionic acid, butyric acid, valeric acid, hexanoic acid, acetic anhydride, o-dichlorobenzene and chlorobenzene, and a mixture thereof.

Embodiment A69. The method of Embodiment A68 wherein the wash solvent is selected from acetic acid, propionic acid and hexanoic acid, and a mixture thereof.

Embodiment A70. The method of Embodiment A69 wherein the wash solvent is selected from acetic acid and propionic acid, and a mixture thereof.

Embodiment A71. The method of Embodiment A65 or A66 wherein the wash solvent is selected from acetic acid, and a mixture of acetic acid with water.

Embodiment A72. The method of Embodiment A71 wherein the wash solvent is a mixture of acetic acid with water.

Embodiment A73. The method of Embodiment A72 wherein the wash solvent is a mixture of at least 50% acetic acid with water.

Embodiment A74. The method of Embodiment A73 wherein the wash solvent is a mixture of at least 75% acetic acid with water.

Embodiment A75. The method of any one of Embodiments A65 through A74 wherein the wash solvent is the same as the reaction solvent (i.e. the wash solvent is the same as the solvent described in any of Embodiments A2 through A13).

Embodiment A76. The method of any one of Embodiments A65 through A67 wherein the wash solvent is acetic acid.

Embodiment A77. The method of any one of Embodiments A65 through A67 wherein the wash solvent is water.

Embodiment A78. The method of any one of Embodiments A64 through A77 further comprising step v) purifying the isolated 3-methyl-2-nitrobenzoic acid (2) by recrystallizing said isolated 3-methyl-2-nitrobenzoic acid (2).

Embodiment A79. The method of any one of Embodiments A64 through A77 further comprising step v) purifying the isolated 3-methyl-2-nitrobenzoic acid (2) by recrystallizing said isolated 3-methyl-2-nitrobenzoic acid (2) from acetic acid or a mixture comprising acetic acid and water.

Embodiment A80. The method of any one of Embodiments A64 through A77 further comprising step v) purifying the isolated 3-methyl-2-nitrobenzoic acid (2) by recrystallizing said isolated 3-methyl-2-nitrobenzoic acid (2) from acetic acid or a mixture of acetic acid and water or a mixture of acetic acid, water and an alkali metal hydroxide.

Embodiment A81. The method of any one of Embodiments A64 through A77 further comprising step v) purifying the isolated 3-methyl-2-nitrobenzoic acid (2) by recrystallizing said isolated 3-methyl-2-nitrobenzoic acid (2) from acetic acid or a mixture of acetic acid, water and sodium hydroxide.

Embodiment A82. The method of any one of Embodiments A64 through A77 further comprising step v) purifying the isolated 3-methyl-2-nitrobenzoic acid (2) by dissolving said isolated 3-methyl-2-nitrobenzoic acid (2) in base and precipitating 3-methyl-2-nitrobenzoic acid (2) by adding acid.

Embodiment A83. The method of any one of Embodiments A64 through A77 further comprising step v) purifying the isolated 3-methyl-2-nitrobenzoic acid (2) by dissolving said isolated 3-methyl-2-nitrobenzoic acid (2) in aqueous sodium hydroxide and precipitating 3-methyl-2-nitrobenzoic acid (2) by adding aqueous hydrochloric acid.

Embodiment A84. The method of any one of Embodiments A64 through A83 wherein the filtering further comprises recycling the filtrate of step iv).

Embodiment A85. The method of Embodiment A84 wherein the filtering further comprises concentrating the filtrate of step iv) and recycling the concentrated filtrate.

Embodiment A86. The method of any one of Embodiments A1 through A85 wherein step vi) further comprises adding the filtrate resulting from step iv) as described in Embodiment A64 (i.e. the mother liquor) is used directly in a subsequent oxidation run after combination with additional 1,3-dimethyl-2-nitrobenzene (1) and optional additional metal catalyst.

Embodiment A87. The method of any one of Embodiments A1 through A86 wherein step vi) further comprises adding the filtrate resulting from step iv) as described in either Embodiment 65A or Embodiment 66A (i.e. the mother liquor and the wash solvent filtrate) are both used directly in a second oxidation run after combining with additional 1,3-dimethyl-2-nitrobenzene (1) and optional additional metal catalyst.

Embodiment A88. The method of Embodiment A1 wherein 1,3-dimethyl-2-nitrobenzene (1) in step i) is optionally dissolved in a solvent; the metal catalyst is a cobalt(II), cobalt(III), manganese(II), manganese(III), iron(II) or iron(III) metal catalyst; the heating is to a temperature of at least about 60° C.; the pressurizing is from about 0.345e+006 N/m² to about 6.89e+006 N/m²; the initiator is acetaldehyde, propionaldehyde, metaldehyde, paraldehyde or methylethylketone; and the oxygen source comprises air, a carrier gas enriched with oxygen gas, or oxygen gas.

Embodiment A89. The method of Embodiment A88 wherein the metal catalyst is a cobalt(II) or cobalt(III) metal catalyst; the heating is to a temperature of at least about 70° C.; the pressurizing is from about 2.07e+006 N/m² to about 4.83e+006 N/m²; the oxygen source comprises air or a carrier gas enriched with oxygen gas; and the oxidizing is less than 90 mol %.

Embodiment A90. The method of Embodiment A89 wherein the solvent is selected from a non-oxidizeable solvent, and a mixture thereof; the metal catalyst is cobalt(II) acetate tetrahydrate; the heating is to a temperature not greater than about 150° C.; the pressurizing is from about 2.76e+006 N/m² to about 4.14e+006 N/m²; the initiator is acetaldehyde; and the oxygen source comprises air.

Embodiment A91. The method of Embodiment A90 wherein the solvent is a mixture of acetic acid with water; the pressure is about 3.45e+006 N/m²; and the heating is to a temperature not greater than about 110° C.

Embodiment B0. A method for preparing a compound of Formula 7

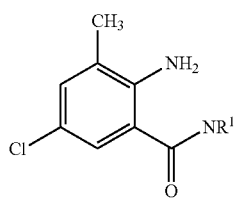

7 wherein $R^1$ is $C_1$-$C_7$ alkyl, $C_3$-$C_6$ cycloalkyl or $C_4$-$C_7$ alkylcycloalkyl; the method characterized by using 3-methyl-2-nitrobenzoic acid (2) as prepared by the method of claim 1.

Embodiment B1. A method for preparing a compound of Formula 7

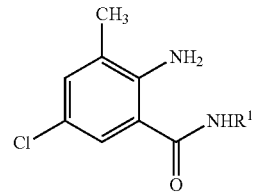

7 wherein $R^1$ is $C_1$-$C_7$ alkyl, $C_3$-$C_6$ cycloalkyl or $C_4$-$C_7$ alkylcycloalkyl;
from 6-chloro-8-methyl-2H-3,1-benzoxazine-2,4(1H)-dione (6)

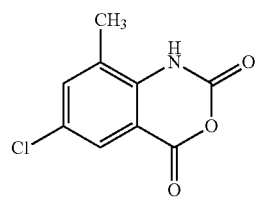

6 in the presence of $R^1NH_2$;
from a compound of Formula 5

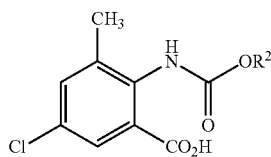

5 wherein $R^2$ is $C_1$-$C_6$ alkyl or $C_3$-$C_6$ alkenyl, each optionally substituted with up to 3 halogen and up to 1 phenyl;
in the presence of a cyclizing agent;
from a compound of Formula 4

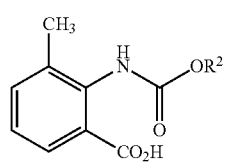

4 in the presence of HCl and $H_2O_2$;
from 2-amino-3-methylbenzoic acid (3)

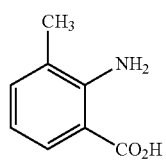

3 in the presence of R²OC(=O)Cl;
from 3-methyl-2-nitrobenzoic acid (2) in the presence of a reducing agent;
characterized by 3-methyl-2-nitrobenzoic acid (2) prepared by the method described in any of Embodiments A1 through A87.

Embodiment B2. The method of Embodiment B1 wherein R¹ is $C_1$-$C_4$ alkyl or $C_3$-$C_6$ cycloalkyl.

Embodiment B3. The method of Embodiment B2 wherein R¹ is methyl, isopropyl, cyclopropyl or t-butyl.

Embodiment B4. The method of Embodiment B3 wherein R¹ is methyl or t-butyl.

Embodiment B5. The method of Embodiment B4 wherein R¹ is methyl.

Embodiment B6. The method of Embodiment B4 wherein R¹ is t-butyl.

Embodiment B7. The method of any one of Embodiments B1 through B6 wherein R² is $C_1$-$C_4$ alkyl.

Embodiment B8. The method of Embodiment B7 wherein R² is methyl or ethyl.

Embodiment B9. The method of Embodiment B8 wherein R² is ethyl.

Embodiment B10. The method of any one of Embodiments B1 through B9 wherein the cyclizing agent is $PBr_3$.

Embodiment C0. A method for preparing a compound of Formula 11

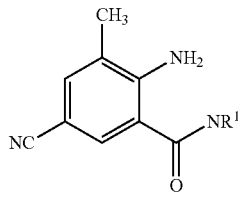

11 wherein R¹ is $C_1$-$C_7$ alkyl, $C_3$-$C_6$ cycloalkyl or $C_1$-$C_4$ alkylcycloalkyl; the method characterized by using 3-methyl-2-nitrobenzoic acid (2) as prepared by the method of claim 1.

Embodiment C1. A method for preparing a compound of Formula 11

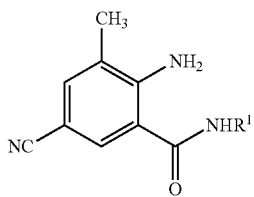

11 wherein R¹ is $C_1$-$C_7$ alkyl, $C_3$-$C_6$ cycloalkyl or $C_4$-$C_7$ alkylcycloalkyl;
from a compound of Formula 10

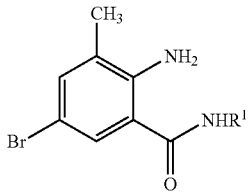

10 in the presence of a cyanide donor;
from a compound of Formula 9

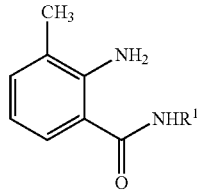

9 in the presence of bromine;
from a compound of Formula 8

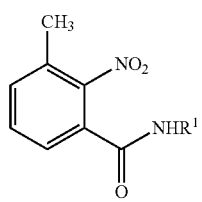

8 in the presence of a reducing agent
from 3-methyl-2-nitrobenzoic acid (2) by successive treatment with an activating agent and $R^1NH_2$; characterized by 3-methyl-2-nitrobenzoic acid (2) prepared by the method described in any of Embodiments A1 through A87.

Embodiment C2. The method of Embodiment C1 wherein R¹ is $C_1$-$C_4$ alkyl or $C_3$-$C_6$ cycloalkyl.

Embodiment C3. The method of Embodiment C2 wherein R¹ is methyl, isopropyl, cyclopropyl or t-butyl.

Embodiment C4. The method of Embodiment C3 wherein R¹ is methyl or t-butyl.

Embodiment C5. The method of Embodiment C4 wherein R¹ is methyl.

Embodiment C6. The method of Embodiment C4 wherein R¹ is t-butyl.

Another aspect of the present invention relates to:
Embodiment F1. A method for preparing a compound of Formula 2

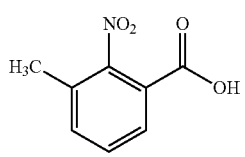

2 comprising, contacting a compound of Formula 1

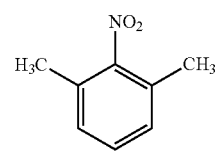

1 with an oxygen source and an initiator provided that less than 99% of a compound of Formula 1 is oxidized.

Embodiment F2. The method of Embodiment F1 wherein the oxygen source comprises air, a carrier gas enriched with air, a carrier gas enriched with oxygen gas or oxygen gas.

Embodiment F3. The method of Embodiment F2 wherein the oxygen source comprises air or a carrier gas enriched with air.

Embodiment F4. The method of Embodiment F3 wherein the oxygen source comprises air.

Embodiment F5. The method of any one of Embodiments F1 through F4 wherein the initiator comprises acetaldehyde, propionaldehyde, metaldehyde, paraldehyde or methylethylketone, or mixtures thereof.

Embodiment F6. The method of Embodiment F5 wherein the initiator comprises acetaldehyde, propionaldehyde or paraldehyde, or mixtures thereof.

Embodiment F7. The method of Embodiment F6 wherein the initiator comprises acetaldehyde.

Embodiment F8. The method of any one of Embodiments F1 through F7 wherein the compound of Formula 1, the oxygen source and the initiator are contacted in the presence of a suitable solvent.

Embodiment F9. The method of Embodiment F8 wherein the suitable solvent comprises acetic acid, propionic acid, butyric acid, valeric acid, hexanoic acid, 2-ethylhexanoic acid, acetic anhydride, o-dichlorobenzene or chlorobenzene, or mixtures thereof.

Embodiment F10. The method of Embodiment F9 wherein the suitable solvent comprises acetic acid, propionic acid, hexanoic acid or 2-ethylhexanoic acid, or mixtures thereof.

Embodiment F11. The method of Embodiment F10 wherein the suitable solvent comprises acetic acid.

Embodiment F12. The method of any one of Embodiments F1 through F11 wherein the suitable solvent further comprises water.

Embodiment F13. The method of Embodiment F12 wherein the suitable solvent comprises acetic acid or a mixture of acetic acid and water.

Embodiment F14. The method of Embodiment F13 wherein the suitable solvent comprises a mixture of acetic acid and water.

Embodiment F15. The method of Embodiment F14 wherein the suitable solvent comprises a mixture of less than 10 wt % water in acetic acid.

Embodiment F16. The method of Embodiment F15 wherein the suitable solvent comprises a mixture of less than 5 wt % water in acetic acid.

Embodiment F77. The method of Embodiment F16 wherein the suitable solvent comprises a mixture of less than 1 wt % water in acetic acid.

Embodiment F18. The method of any one of Embodiments F1 through F17 wherein the weight % of the compound of Formula 1 in the suitable solvent is from about 4% to about 90%.

Embodiment F19. The method of Embodiment F18 wherein the weight % of the compound of Formula 1 in the suitable solvent is from about 4% to about 80%.

Embodiment F20. The method of Embodiment F19 wherein the weight % of the compound of Formula 1 in the suitable solvent is from about 4% to about 70%.

Embodiment F21. The method of Embodiment F19 wherein the weight % of the compound of Formula 1 in the suitable solvent is from about 20% to about 75%.

Embodiment F22. The method of Embodiment F20 wherein the weight % of the compound of Formula 1 in the suitable solvent is from about 20% to about 60%.

Embodiment F23. The method of Embodiment F21 wherein the weight % of the compound of Formula 1 in the suitable solvent is from about 40% to about 70%.

Embodiment F24. The method of Embodiment F22 wherein the weight % of the compound of Formula 1 in the suitable solvent is from about 30% to about 50%.

Embodiment F25. The method of Embodiment F23 wherein the weight % of the compound of Formula 1 in the suitable solvent is about 67%.

Embodiment F26. The method of Embodiment F24 wherein the weight % of the compound of Formula 1 in the suitable solvent is about 50%.

Embodiment F27. The method of any one of Embodiments F1 through F26 wherein the mixture formed by contacting the compound of Formula 1, the oxygen source and the initiator is heated to a temperature of about 60° C. to about 150° C.

Embodiment F28. The method of Embodiment F27 wherein the mixture is heated to a temperature of about 80° C. to about 120° C.

Embodiment F29. The method of Embodiment F28 wherein the mixture is heated to a temperature of about 90° C. to about 115° C.

Embodiment F30. The method of Embodiment F29 wherein the mixture is heated to a temperature of about 100° C.

Embodiment F31. The method any one of Embodiments F1 through F30 wherein the mixture formed by contacting the compound of Formula 1, the oxygen source and the initiator is pressurized from about 1400 kPa (about 200 p.s.i.g or 0.345e+006 newtons/meter$^2$) to about 6900 kPa (about 1000 p.s.i.g or 6.89e+006 newtons/meter$^2$).

Embodiment F32. The method of Embodiment F31 wherein the mixture is pressurized from about 1700 kPa (about 250 p.s.i.g. or 1.72e+006 newtons/meter$^2$) to about 5200 kPa (about 750 p.s.i.g or 5.17e+006 newtons/meter$^2$).

Embodiment F33. The method of Embodiment F32 wherein the mixture is pressurized from about 2100 kPa (about 300 p.s.i.g. or 2.07e+006 newtons/meter$^2$) to about 4800 kPa (about 700 p.s.i.g or 4.83e+006 newtons/meter$^2$).

Embodiment F34. The method of Embodiment F33 wherein the mixture is pressurized from about 2800 kPa (about 400 p.s.i.g.or 2.76e+006 newtons/meter$^2$) to about 4100 kPa (about 600 p.s.i.g or 4.14e+006 newtons/meter$^2$).

Embodiment F35. The method of Embodiment F34 wherein the mixture is pressurized to about 3500 kPa (about 500 p.s.i.g or 3.45e+006 newtons/meter$^2$).

Embodiment F36. The method of any one of Embodiments F1 through F35 wherein less than about 90% of a compound of Formula 1 is oxidized (less than about 90% of a compound of Formula 1 is converted).

Embodiment F37. The method of Embodiment F36 wherein less than about 80% of a compound of Formula 1 is oxidized (less than about 80% of a compound of Formula 1 is converted).

Embodiment F38. The method of Embodiment F37 wherein less than 70% of a compound of Formula 1 is oxidized (less than about 70% of a compound of Formula 1 is converted).

Embodiment F39. The method of Embodiment F38 wherein less than 60% of a compound of Formula 1 is oxidized (less than about 60% of a compound of Formula 1 is converted).

Embodiment F40. The method of Embodiment F39 wherein less than 50% of a compound of Formula 1 is oxidized (less than about 50% of a compound of Formula 1 is converted).

Embodiment F41. The method of Embodiment F40 wherein less than 40% of a compound of Formula 1 is oxidized (less than about 40% of a compound of Formula 1 is converted).

Embodiment F42. The method of Embodiment F41 wherein less than 30% of a compound of Formula 1 is oxidized (less than about 30% of a compound of Formula 1 is converted).

Embodiment F43. The method of Embodiment F42 wherein less than 20% of a compound of Formula 1 is oxidized (less than about 20% of a compound of Formula 1 is converted).

Embodiment F44. The method of any one of Embodiments F1 through F43 wherein the selectivity is greater than 40%.

Embodiment F45. The method of Embodiment F44 wherein the selectivity is greater than 50%.

Embodiment F46. The method of Embodiment F45 wherein the selectivity is greater than 60%.

Embodiment F47. The method of Embodiment F46 wherein the selectivity is greater than 70%.

Embodiment F48. The method of Embodiment F47 wherein the selectivity is greater than 80%.

Embodiment F49. The method of Embodiment F48 wherein the selectivity is greater than 90%.

Embodiment F50. The method of any one of Embodiments F1 through F49 further comprising isolating the compound of Formula 2 by filtering and optionally washing with a wash solvent.

Embodiment F51. The method of any one of Embodiments F1 through F50 wherein the wash solvent comprises at least one solvent selected from acetic acid, propionic acid, butyric acid, valeric acid, hexanoic acid, acetic anhydride, o-dichlorobenzene and chlorobenzene, and mixtures thereof.

Embodiment F52. The method of Embodiment F51 wherein the wash solvent further comprises water.

Embodiment F53. The method of Embodiments F51 and F52 wherein the wash solvent comprises acetic acid or a mixture of acetic acid and water.

Embodiment F54. The method of any one of Embodiments F1 through F53 further comprising isolating the compound of Formula 2 by filtering and purifying the isolated compound of Formula 2 by recrystallizing from a recrystallization solvent.

Embodiment F55. The method of any one of Embodiments F1 through F54 wherein the recrystallization solvent comprises acetic acid or a mixture of acetic acid and water or a mixture of acetic acid, water and an alkali metal hydroxide.

Embodiment F56. The method of any one of Embodiments F1 through F53 further comprising isolating the compound of Formula 2 by filtering and purifying the isolated compound of Formula 2 by dissolving in aqueous base followed by precipitating by adding aqueous acid.

Embodiment F57. The method of Embodiment F56 wherein the aqueous base is aqueous sodium hydroxide and the aqueous acid is aqueous hydrochloric acid.

Embodiment F58. The method of any one of Embodiments F1 through F53 wherein the isolating the compound of Formula 2 by filtering further comprises recycling the filtrate directly in a subsequent oxidation run after combination with additional 1,3-dimethyl-2-nitrobenzene (1) and solvent.

DETAILED DESCRIPTION OF THE INVENTION

The present invention is a process to selectively oxidize 1,3-dimethyl-2-nitrobenzene (a compound of Formula 1) to 3-methyl-2-nitrobenzoic acid (a compound of Formula 2). Selectively oxidizing one aryl methyl group in the presence of two aryl methyl groups (in the compound of Formula 1) is accomplished by partial conversion of the starting compound of Formula 1 (i.e. stopping the reaction before all the compound of Formula 1 is reacted). Partial conversion enables the production of the mono-oxidation product (the compound of Formula 2) with minimal contamination of the di-oxidation product (2-nitro-1,3-benzenedicarboxylic acid, compound of Formula 13).

The present process provides for the selective oxidation of the compound of Formula 1 comprising, contacting a compound of Formula 1 with an oxidation catalyst in the presence of an oxygen source and an initiator provided that less than 99% of a compound of Formula 1 is oxidized. A representative chemical equation for the oxidation method is shown below. A representative initiator (acetaldehyde) is also shown as part of the oxidation process.

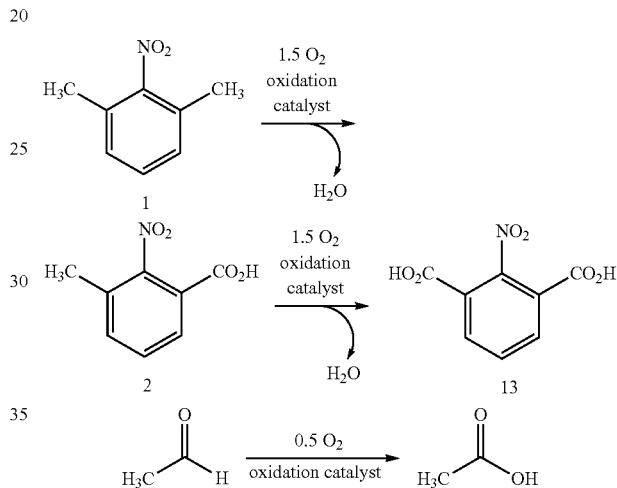

The oxidation catalyst (alternatively called the metal catalyst) suitable for use in the present process include metal salts of cobalt (II), cobalt(III), manganese(II), manganese (III), iron(II), iron(III) or zirconium(IV), or mixtures thereof. Preferred oxidation catalysts comprise cobalt(II), cobalt(III), manganese(II), manganese(III), iron(II) or iron (III) salts, or mixtures thereof. Examples of suitable salts include acetate, propionate, butyrate, carbonate, oxide and hydroxide. Particularly suitable oxidation catalysts comprise cobalt(II) acetate, cobalt(II) acetate tetrahydrate or cobalt(II) carbonate. Cobalt(II) acetate tetrahydrate is especially useful and economical.

The amount of oxidation catalyst useful for the present process can vary over a relatively wide range. The weight percent of the oxidation catalyst (metal catalyst) to the compound of Formula 1 can range from about 0.01% to about 20%. A very useful weight percent of the oxidation catalyst to the compound of Formula 1 is from about 0.5% to about 7%. A particularly useful weight percent of the oxidation catalyst to the compound of Formula 1 is from about 1% to about 3%.

The oxygen source suitable for the present invention can be air, a carrier gas enriched with air, a carrier gas enriched with oxygen gas or pure oxygen gas. An example of an appropriate unreactive carrier gas is nitrogen gas. Air is an especially preferred oxygen source for economy reasons. The oxygen source is most typically introduced below the surface of the reaction mixture via a multiport distribution tube or a dip tube. The oxygen source can be introduced into the reaction at ambient temperature or it can be preheated to close to the reaction temperature so as to not provide a source of cooling during the reaction. The flow rate of the oxygen source can be varied and can be used to moderate reaction rate.

The initiator works as a "promoter" along with the oxidation catalyst. A mechanism has been suggested wherein the initiator/promotor works to maintain the oxidation catalyst in an "active" oxidation state (Jacobson and Ely, *Chemical Industries* 1996, 68, 87-96). The initiator is generally selected from an aliphatic aldehyde or ketone such as acetaldehyde, proprionaldehyde, paraldehyde, metaldehyde or methyl ethylketone. Acetaldehyde is especially useful because of its availability and low cost. In an embodiment of the present invention the acetaldehyde initiator reacts with the Co(II) oxidation catalyst converting it to Co(III). The Co(III) oxidation catalyst generates peroxy radicals which can initiate hydrogen atom abstraction mediating the oxidation of the methyl group on the starting compound of Formula 1. The acetaldehyde is oxidized to acetic acid which is not detrimental to the oxidation reaction. No oxidation reaction will occur if the initiator is left out of the present invention. The initiator is supplied continuously throughout the reaction and is most typically introduced below the surface of the reaction mixture via a multiport distribution tube or a dip tube. The initiator can be introduced as a liquid or in solution with an optional oxidation resistant solvent. The flow rate of the initiator can be varied and can be used to moderate reaction rate.

The present invention can be run in the absence of a solvent or in the presence of a suitable solvent. The optional solvent should be oxidation resistant (i.e. a solvent whose rate of oxidation is substantially slower than that of the compounds of Formula 1 and 2) and suitable for suspending, or, preferably dissolving the reactants. Aliphatic carboxylic acids are particularly suitable solvents for the process of this invention. Useful solvents are acetic acid, propionic acid, butyric acid, valeric acid, hexanoic acid, 2-ethylhexanoic acid, acetic anhydride, o-dichlorobenzene and chlorobenzene, and mixtures thereof. Especially useful solvents are acetic acid, propionic acid, hexanoic acid and 2-ethylhexanoic acid and mixtures thereof. Acetic acid is a preferred solvent for reasons of economy, availability and environmental acceptability. Also the by-product of using acetaldehyde as an initiator (acetic acid) will become part of the solvent. Water can also be optionally added to the reaction mixture. However too much water can slow the oxidation reaction and affect the solubility of the reactants and products. Preferably the water content of the solvent is less than 10 wt %. An especially useful water content of the solvent is less than 1 wt %. Water is a by-product of the oxidation process.

Remarkably, a wide range of concentrations of the starting compound of Formula 1 relative to the solvent are tolerated in the present invention. The present process accommodates the selective oxidation of the compound of Formula 1 in a suitable solvent at a range of about 4 wt % to about 90 wt % [wherein wt % is (the weight of the compound of Formula 1 divided by the combined weight of the compound of Formula 1 plus the solvent)×100]. The higher concentrations are more economical. An especially useful range of weight % of the compound of Formula 1 in the suitable solvent is from about 20% to about 75%. A particularly useful range of weight % of the compound of Formula 1 in the suitable solvent is from about 40% to about 70%. The selectively of the oxidation is unexpectedly high throughout the useful ranges tested.

In an embodiment of the present process the compound of Formula 1 is selectively oxidized under pressure and at elevated temperature. The optimal operating temperature of the present invention is from about 60° C. to about 150° C. The reaction is very slow at the lower temperature and potentially less selective at the higher temperature because of increased side reactions. A useful temperature range is from about 80° C. to about 120° C. An especially useful temperature range is from about 90° C. to about 115° C.

The pressure range of the present reaction is primarily determined by safety concerns of working with flammable solvents and initiator in the presence of oxygen. The pressure range can vary depending on the flash point of the solvent. Higher pressures decrease the amount of solvent in the head space over the reaction. The pressure can range from about 200 p.s.i.g. (1.38e+006 N/m$^2$ or about 1400 kPa) to about 1000 p.s.i.g. (6.89e+006 N/m$^2$ or about 6900 kPa). A useful range of pressure is from about 250 p.s.i.g. (1.72e+006 N/m$^2$ or about 1700 kPa) to about 750 p.s.i.g. (5.17e+006 N/m$^2$ or about 5200 kPa). A very useful range of pressure is from about 300 p.s.i.g. (2.07e+006 N/m$^2$ or about 2100 kPa) to about 700 p.s.i.g. (4.83e+006 N/m$^2$ or about 4800 kPa). An especially useful range of pressure is from about 400 p.s.i.g. (2.76e+006 N/m$^2$ or about 2800 kPa) to about 600 p.s.i.g. (4.14e+006 N/m$^2$ or about 4100 kPa), or about 500 p.s.i.g (3.45e+006 N/m$^2$ or about 3500 kPa). The reaction vessel is usually pressurized at the start of the reaction with nitrogen gas and then is replaced with air to begin the reaction. Operating at high pressures increases the concentration of oxygen dissolved in the reaction mixture.

In order to obtain an optimum yield in this process, the conversion of the compound of Formula 1 is controlled so that less than 99% of the compound of Formula 1 is oxidized. Although not critical to operability, optimal process productivity prefers the conversion of the compound of Formula 1 to be at least about 10% (at least 10% of the compound of Formula 1 is oxidized). It is preferable to control the conversion of the compound of Formula 1 to be less than about 90%. It is more preferable to control the conversion of the compound of Formula 1 to be less than about 70%. In order to obtain optimum selectivity, it preferable to control the conversion of the compound of Formula 1 to be less than about 50% (less than 50% of a compound of Formula 1 is oxidized). Controlling the conversion of the compound of Formula 1 provides the compound of Formula 2 in high selectivity.

The process can be carried out in a well mixed pressure vessel to which the 1,3-dimethyl-2-nitrobenzene (1), metal catalyst, the optional solvent, and optional water are first added. The pressure reactor can be made of conventional materials such as stainless steel or Hastelloy® which are compatible with the reactants and catalyst. Reactors used for this process are often equipped with agitator and temperature controls by an oil heating unit that circulates hot oil in the reactor jacket and/or an internal coil. In general, the compound of Formula 1, the metal catalyst, the optional solvent, and optional water can be charged to a suitable reactor, the reactor pressurized with an inert gas such as nitrogen, the mixture heated to the desired reaction temperature. Once the reactor contents are at the desired temperature, the continuous flow of the oxygen source and initiator can be started. An induction period of about 5 to 30 min is normal, marked by a rapid increase in temperature of about 5 to about 10° C. which can be controlled by appropriate adjustments of the reactor heating and cooling system to maintain the reaction temperature within the desired range. The oxidation reactor for the present invention should be equipped with a high pressure sample line that allows sampling of the reaction mixture during operations. Percent conversion of the starting material and production of impurities can be monitored by gas chromatography analysis. The reaction is terminated when the desired level of conversion of the starting compound of Formula 1 is reached. The reaction is terminated by stopping the flow of the oxygen source and initiator to the reactor, and is followed by a nitrogen purge of the reaction mixture. The mixture is optionally cooled and depressurized prior to isolation of the product.

The compound of Formula 2 can be isolated by a variety of methods. After an optional partial concentration, the reaction mixture can be cooled to crystallize the compound of Formula 2. The product can be recovered by filtration and optionally washed with the reaction solvent (if one was used) or, alternatively with aqueous acetic acid, followed by a water wash. To minimize product loss during washing, the filter cake may also be washed with a solvent, such as hexanes or heptanes, in which the compound of Formula 2 is poorly soluble and the compound of Formula 1 is freely soluble. The isolated solid can then be dried or, if it is to be further purified, processed as a wet cake.

Filtrates and washes may be further processed to recover starting material, product, catalyst and solvent contained therein. For example, the mother liquor (i.e. the filtrate from the first isolation filtration) can be concentrated under vacuum to recover solvent and by-product acetic acid for reuse or further purification. The residual material can then be cooled to provide a second crop of the compound of Formula 2 (which can be washed and dried in the same manner as the first crop) and enable recovery of ureacted compound of Formula 1.

If desired, the isolated compound of Formula 2 can be recrystallized from a solvent such as a carboxylic acid or a mixture of a carboxylic acid acid and water. Glacial acetic acid and aqueous acetic acid are particularly useful for recrystallizing the compound of Formula 2 to provide high-purity product. The recrystallized product can be recovered by filtration and optionally washed with recrystallization solvent and/or water. When recrystallizing the compound of Formula 2 containing the compound of Formula 13 (2-nitro-1,3-benzenedicarboxylic acid) it is advantageous to add a small amount of sodium hydroxide or other base to reduce the amount of the compound of Formula 13 that co-crystallizes with the compound of Formula 2.

The compound of Formula 2 may also be purified by first dissolving in an aqueous base (e.g. aqueous sodium carbonate) and then adding an acid (e.g. aqueous hydrochloric acid) to precipitate the desired compound of Formula 2. The precipitated product can be recovered by filtration and optionally washed with recrystallization solvent and/or water.

The mother liquor (filtrate) obtained after isolation of the compound of Formula 2 comprises unreacted compound of Formula 1, compound of Formula 2, catalyst, solvent, water and impurities. Oxidation catalysts such as cobalt acetate can be recovered by methods known in the literature, for example by treatment of the cobalt acetate solutions with a sodium carbonate solution followed by filtration to recover cobalt carbonate.

As the present oxidation process involves limiting the conversion of the compound of Formula 1, it is desirable that the unreacted compound of Formula 1 be recovered or directly re-used. Two possible routes may be used to recover unreacted compound of Formula 1. First, fractional distillation of the filtrate from the product recovery process under partial pressure sample can be used to isolate unreacted compound of Formula 1. It is noted, however, that compound of Formula 2 is thermally unstable and distillation of crude compound of Formula 1 in the presence of the compound of Formula 2 must be carried out with caution. A pre-treatment process (e.g. aqueous extraction) process to remove residual compound of Formula 2 may be required before distillation. The second route is to simply re-introduce the fitrate containing the compound of Formula 1 directly back into the oxidation process. In this route, the filtrate may be reformulated with additional fresh compound of Formula 1 and cobalt(II) acetate tetrahydrate (optionally in a solvent). The reformulated mixture may then be used directly in the oxidation process or concentrated prior to use to give the desired concentration of the compound of Formula 1 and/or to remove water. Direct recycle of the compound of Formula 1 is possible due to the high selectivity of the oxidation process. After several experiments (or passes) through the oxidation process, it may be necessary to distill the compound of Formula 1 to remove impurities that build-up through repeated recycle.

Another aspect of the present invention relates to a method of preparing a compound of Formula 2 comprising, contacting a compound of Formula 1 with an oxygen source and an initiator provided that less than 99% of a compound of Formula 1 is oxidized. This method of oxidation does not require the presence of an oxidation catalyst and is demonstrated in Example 18. The catalyst-free method can also involve one or more recycle steps. The recycle in the catalyst-free oxidation process involves limiting the conversion of the compound of Formula 1, filtering to remove the compound of Formula 2 and recovering or directly re-using the unreacted compound of Formula 1 in another catalyst-free oxidation process. Although the oxidation catalyst improves the selectivity and productivity of the present invention relative to an oxidation catalyst-free method, the present invention can be utilized without the presence of an oxidation catalyst.

One or more of the following methods and variations as described in Schemes 1-11 can be used to prepare the compounds of Formulae 7 and 11. The definitions of $R^1$ in the compounds of Formulae 7, 8, 9, 10 and 11; and in the compound of Formula $R^1NH_2$ below are as defined above in the Summary of the Invention unless otherwise noted. The definitions of $R^2$ in the compounds of Formulae 4 and 5; and in the compound of Formula $R^2OC(=O)Cl$ below are as defined above in Embodiment B1 unless otherwise noted. The compound of Formula 7A is a subset of a compound of Formula 7, and all substituents for Formula 7A are as defined above for a compound of Formula 7.

As described in the Summary of the Invention, another aspect of the present invention relates to compounds that can be prepared from the compound of Formula 2 (characterized by using the compound of Formula 2 as prepared by the method described for the oxidation of a compound of Formula 1 in the Summary of the Invention). For example, the compound of Formula 2 can ultimately be used to prepare the compounds of Formula 7 and 11 as described in the Schemes 1 through 11 below. The compound of Formulae 7 and 11 are, in turn, useful intermediates in certain insecticides described in Examples 7 through 20 in WO 2006/062978. In particular, compounds such as A (chlorantraniliprole), B (cyantraniliprole), C (tetraniliprole) and D shown below can be prepared from a compound of Formula 7 or 11 prepared from the compound of Formula 2 (characterized by using the compound of Formula 2 as prepared by the method described for the oxidation of a compound of Formula 1 in the Summary of the Invention)

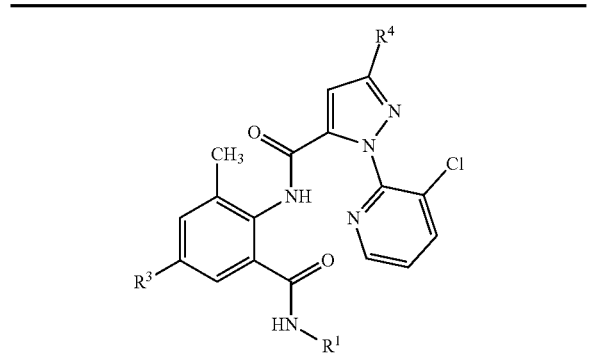

| Compound | R¹   | R³ | R⁴                                      |
|----------|------|----|-----------------------------------------|
| A        | CH₃  | Cl | Br                                      |
| B        | CH₃  | CN | Br                                      |
| C        | CH₃  | CN | [5-(trifluoromethyl)-2H-tetrazol-2-yl]methyl |
| D        | t-Bu | Cl | —OCFH₂                                  |

As shown below in Scheme 1, a compound of Formula 7 can be prepared from the corresponding compound of Formula 6 (6-chloro-8-methyl-2H-3,1-benzoxazine-2,4(1H)-dione) wherein the amine of Formula R¹NH₂ can be used as a ring-opening reagent. This transformation is described in Example 1 of WO2006/062978, and Examples 2 through 5 of WO2008/010897.

Scheme 1

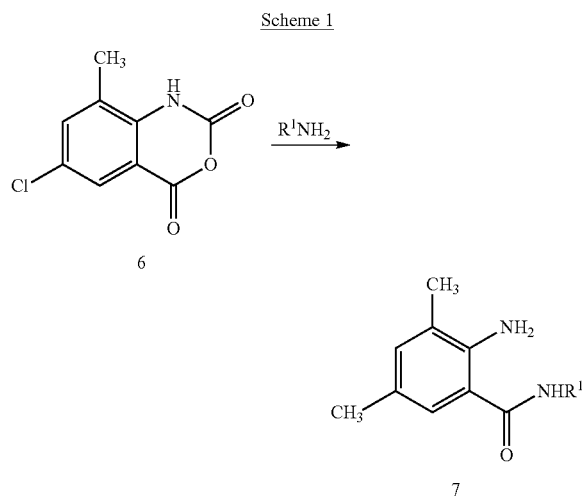

As shown in Scheme 2, the compound of Formula 6 can be prepared from a compound of Formula 5. The formation of the compound of Formula 6 can be accomplished by contacting a compound of Formula 5 with a cyclizing agent such as phosphorus tribromide, although many such cyclization agents are known in the literature. Examples of this transformation can be found in Example 1 of WO2008/010897.

Scheme 2

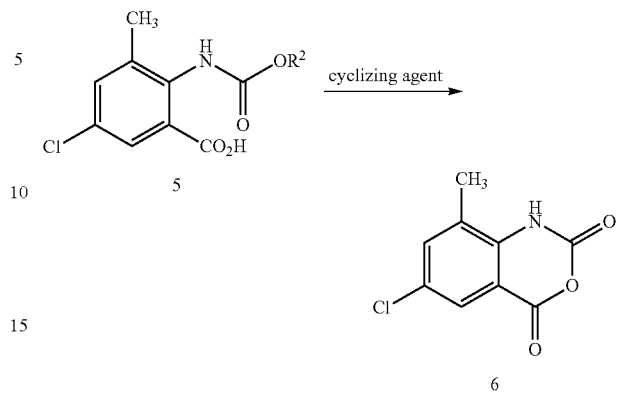

A compound of Formula 5 can be prepared from a compound of Formula 4 as shown in Scheme 3. Formation of a compound of Formula 5 can be accomplished by contacting a compound of Formula 4 with a chlorinating agent. Particularly useful for this chlorination is the use of nascent chlorine generated by contact of aqueous hydrochloric acid with hydrogen peroxide. Chemical transformations of this type are known for example as described in Reference Example 1 in WO2008/010897.

Scheme 3

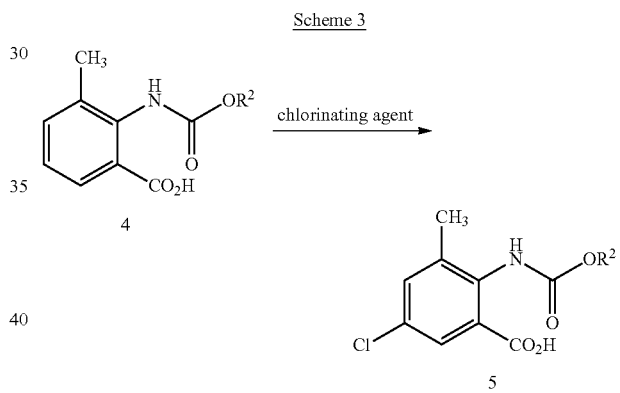

A compound of Formula 4 can be prepared from a compound of Formula 3 (2-amino-3-methylbenzoic acid, also known as 3-methylanthranilic acid) utilizing a variety of chloroformates under basic conditions as shown in Scheme 4. Preparing this type of acylated aniline derivatives is well known in the literature. The formation of compounds of Formula 4 can be accomplished by contacting the compound of Formula 3 with alkyl chloroformates of formula R²OC(=O)Cl. A representative example (where R² is CH₂CH₃) can be found in J. Chem. and Eng. Data 1968, 13(4), 577-9.

Scheme 4

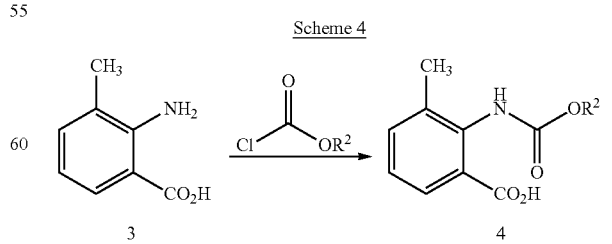

The preparation of the compound of Formula 3 can be achieved either by catalytic or stoichiometric reduction of the compound of Formula 2 prepared as described in the Summary of the Invention. Stoichemetric methods include reduction with zinc in acetic acid. Catalytic methods of reduction include reduction in the presence of a palladium on carbon or platinum oxide catalyst in a hydroxylic solvent such as methanol, ethanol or isopropanol.

Scheme 5

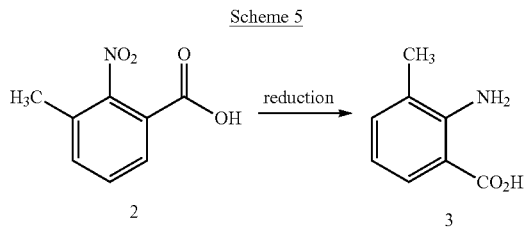

Alternatively, the compound of Formula 6 can be prepared from the compound of Formula 7A (2-amino-5-chloro-3-methylbenzoic acid) as shown in Scheme 6. The compound of Formula 6 can be prepared from the compound of Formula 7A by a variety of known methods that are well documented in the chemical literature. For example, reaction of the compound of Formula 7A with phosgene or a phosgene equivalent can provide the compound of Formula 6 in high yields. For leading references to the methods, see Coppola, Synthesis 1980, 505, and Fabis et al., *Tetrahedron* 1998, 10789. Alternative methods include the use of oxalyl chloride or boc-anhydride (di-t-butyl carbonate).

Scheme 6

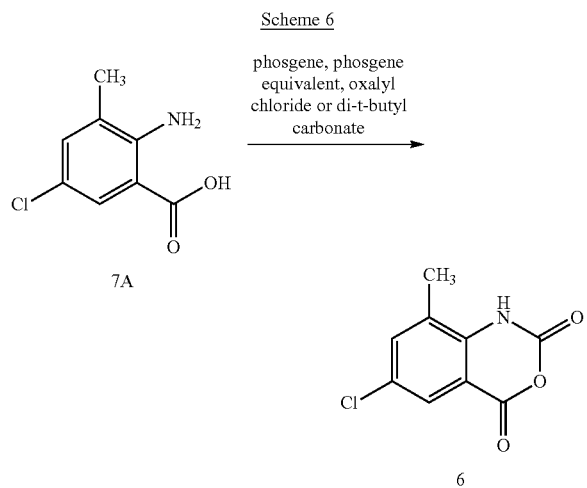

The compound of Formula 7A can, in turn, be prepared from the compound of Formula 3. The formation of the compound of Formula 7A can be accomplished by contacting the compound of Formula 3 with a chlorinating agent such as chlorine, "positive-chlorine" reagents such as trichloroisocyanuric acid and N-chlorosuccinimide as described in Example 2 of WO 2006/062978, and chlorinating reagents such as a mixture comprising hydrogen peroxide and hydrogen chloride.

Scheme 7

A compound of Formula 7 can be prepared from a compound of Formula 9. Formation of a compound of Formula 7 can be accomplished by contacting a compound of Formula 9 with a chlorinating agent such as chlorine, "positive-halogen" reagents such as trichloroisocyanuric acid and N-chlorosuccinimide, and halogenating reagents such as the mixtures comprising hydrogen peroxide and a hydrogen chloride as described in Example 5, Step B in WO 2006/062978.

Scheme 8

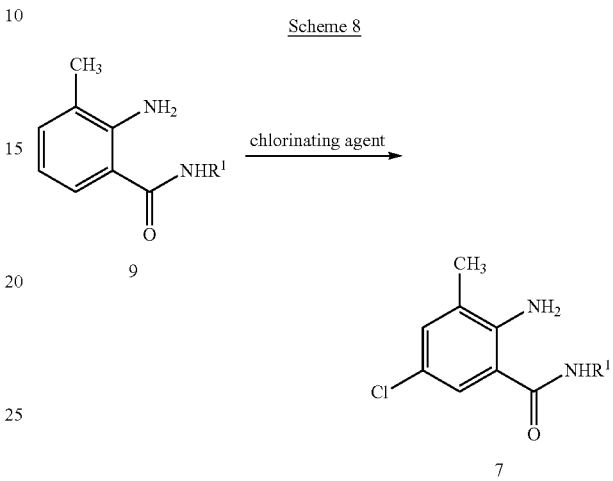

In another aspect of the present invention, the compound of Formula 2 prepared by air oxidation of the compound of Formula 1 as described above, is a useful intermediate for preparing a compound of Formula 11. This intermediate is useful for the synthesis of insecticides as described in Examples 15 through 20 in WO 2006/062978. A compound of Formula 11 can be prepared by cyanation of a compound of Formula 10. The formation of a compound of Formula 11 can be accomplished by contacting a compound of Formula 10 with a cyanating agent or cyanide donor in the presence of i) a catalyst consisting of copper, nickel or palladium; ii) a nitrogen or phosphorous ligand; and iii) an optional source of iodide. Useful procedures for this transformation are described in Example 6, Step B, in WO 2006/062978 as well as in WO 2008/070158, WO 2008/082502, WO 2009/006061, WO 2009/061991, WO 2009/085816, and WO 2009/111553. The formation of a compound of Formula 11 can also be accomplished by contacting a compound of Formula 10 with copper cyanide in a dipolar aprotic solvent using methods that are well known in the art.

Scheme 9

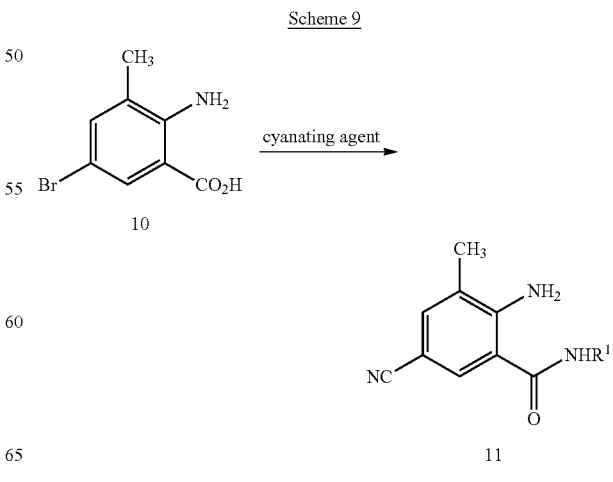

A compound of Formula 10 can be prepared by treatment of a compound of Formula 9 by a variety of brominating agents known in the art as shown in Scheme 10. A method for preparing a compound of Formula 10 involves bromination of a compound of Formula 9 by treatment with a gas containing bromine, as illustrated by the procedure of Reference Example 1 in WO 2008/082502. Alternatively, a compound of Formula 10 can be prepared by bromination of a compound of Formula 9 using a variety of brominating agents known in the literature including bromine and N-bromosuccinimide (NBS) and mixtures comprising hydrogen peroxide and hydrogen bromide. For leading references describing these methods, see Scheme IV and Example 132 of WO 98/16503, Scheme 11 of WO 2006/068669, Scheme 4 and Example 1, Step A in WO 2003/015519, and Scheme 15 and Example 6, Step A in WO 2006/062978.

Scheme 10

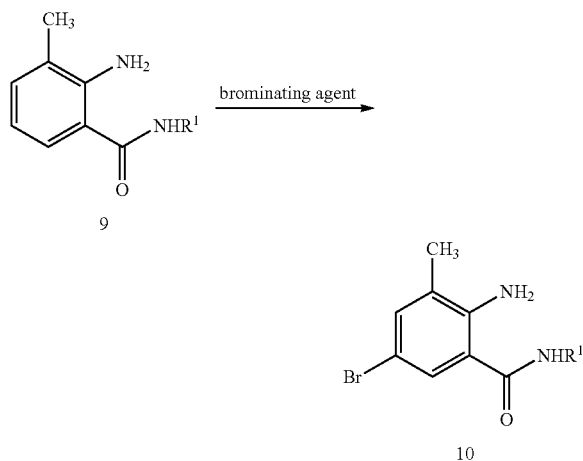

The formation of a compound of Formula 9 can be accomplished by reduction of a compound of Formula 8. Typical reduction procedures involve reduction with hydrogen in the presence of a metal catalyst such as palladium on carbon or platinum oxide in hydroxylic solvents such as methanol, ethanol and isopropanol. For example, see Scheme 1 in *Bioorganic & Medicinal Chemistry Letters* 2005, 15, 4898-4906. This reduction can also be conducted in the presence of zinc in acetic acid. These and other methods for reducing nitro groups are well documented in the chemical literature.

Scheme 11

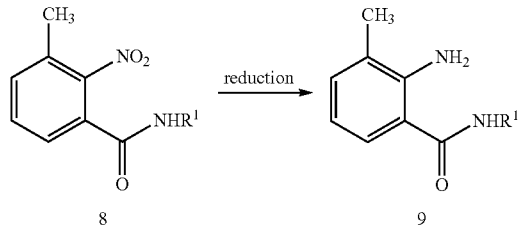

The formation of a compound of Formula 8 can be accomplished by treatment of the compound of Formula 2 with a carboxylic acid activating agent followed by treatment with a primary amine of formula $R^1NH_2$ characterized by the compound of Formula 2 being prepared by the method described in the Summary of the Invention. Carboxylic acid activating agents suitable for use with the compound of Formula 2 include alkyl chloroformates (see, for example, Scheme 1 in *Bioorganic & Medicinal Chemistry Letters* 2005, 15, 4898-4906), thionyl chloride (W02012/00700), and oxalyl chloride (*Bioorganic & Medicinal Chemistry Letters* 2010, 20, 1128-1133). Many other methods for interconversion of carboxylic acids and amides are well documented in the chemical literature.

Alternatively, the formation of a compound of Formula 9 can be accomplished by treatment of a compound of Formula 12 (8-methyl-2H-3,1-benzoxazine-2,4(1H)-dione) with a primary amine of formula $R^1NH_2$ by using procedures such as that described by L. H. Sternbach et al., *J. Org. Chem.* 1971, 36, 777-781 and Example 5, Step A in WO 2006/062978.

Scheme 12

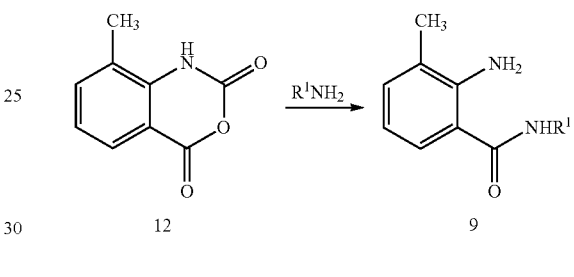

The compound of Formula 12 can be made by the reaction of the compound of Formula 3 with phosgene or a phosgene equivalent or by a variety of methods that are well documented in the chemical literature.

It is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated. The oxidation reactor was equipped with a dip-tube sampling line. Sampling of the reaction mixture during the run allowed the consumption of the compound of Formula 1 and the formation of the compound of Formula 2 to be monitored. Monitoring the reaction was performed using gas chromatograph (e.g., GC) analysis using samples taken from the process diluted in tetrahydrofuran and derivatized with N,O-bis(trimethylsilyl) trifluoracetamide. The GC method gave comparable response factors for the compound of Formula 1, the compound of Formula 2 and the compound of Formula 13. This allowed the GC area % data to be used to calculate component normalized weight fractions. The normalized weight fraction data was then used to calculate mole fractions and reaction molar conversions and selectivities.

GC analysis of the product was performed using a GC (Bruker, Billerica, Mass. 01821) equipped with an FID detector fitted with a Zebron ZB5MSi GC capillary column (Phenomenex, Torrance, Calif. 90501-1430). Column dimensions were 5 m, 1.0 mm film×0.25 mm internal diameter and the temperature program used was 60-300° C. at 25° C./min then held at 300° C. for 0.4 min. In the following Tables "Ex." means Example, "Cony." means Conversion, "Select." means Selectivity, "Calc'd" means Calculated, "(1)" means the compound of Formula 1, "(2)"

means the compound of Formula 2, "(13)" means the compound of Formula 13, "N.D." means not determined and "NAA" means Neutron Activation Analysis.

LC analysis of the product was performed using a LC (Agilent, Santa Clara, Calif. 95051) equipped with a diode array UV detector fitted with a Kinetex 2.6 μm XB-C18 LC column (Phenomenex, Torrance, Calif. 90501-1430). Column dimensions were 4.6 mm×100 mm. The column was maintained at 45° C. The mobile phase was composed of 0.1% v/v acetic acid in water (A) and acetonitrile (B). The mobile phase program was 90% A/10% B for 3 minutes, changed to 20% A/80% B over 12 minutes and then 20% A/80% B for 3 minutes.

EXAMPLES 1-9

Synthesis of 3-methyl-2-nitrobenzoic acid (2) (Runs with 5-50% Loading of 1,3-dimethyl-2-nitrobenzene(1))

A one liter Hastelloy® C-276 pressure reactor was used for oxidation studies using air as the oxygen source. The nitrogen and air supply lines to the reactor were equipped with mass flow meters and valves to control the gas addition rates. The vent line from the reactor was equipped with a valve connected to a pressure transducer for reactor pressure control. The reactor was heated and cooled using an oil system that circulated through the reactor jacket and an internal heat exchange coil. The reactor was also equipped with a mechanical agitator for reaction mixture stirring at 800 rpm. The air was supplied sub-surface into the reaction mixture. The acetaldehyde was supplied sub-surface into the reaction mixture.

In each example, a mixture of cobalt(II) acetate tetrahydrate, 1,3-dimethyl-2-nitrobenzene (compound of Formula 1) and water in acetic acid was prepared and the mixture was added to the pressure reactor. The reactor was sealed, purged with nitrogen and the contents stirred. The reactor was then pressurized with nitrogen to 500 psig (3450 kPa) and heated. As the internal temperature of the reactor approached 100° C., the nitrogen supply was stopped and air was fed at a rate of 2 SLPM (standard liters per minute). Acetaldehyde was then fed to the reactor from a syringe pump at a rate of 40 mL/h. The reaction was strongly exothermic and the reactor jacket temperature was adjusted to maintain the reaction mixture at 100° C.

After addition of each 40 mL aliquot of acetaldehyde, the acetaldehyde and air feeds were temporally stopped and the reactor fed with nitrogen. A sample of the reaction mixture, while still under pressure, was then taken via a reactor sub-surface dip-tube. The nitrogen feed was then stopped and the air and acetaldehyde restarted at the target rates.

After the desired total amount of acetaldehyde was added, acetaldehyde and air feeds were stopped and the reactor purged was with nitrogen. A final sample of the reaction mixture was then collected and the reactor depressurized. The reaction mixture was discharged (while still at about the reaction temperature) from the bottom of the reactor to a product collection vessel.

After allowing the reaction mixture to cool to room temperature (with optional concentration using a rotary evaporator) the 3-methyl-2-nitrobenzoic acid (compound of Formula 2) and 2-nitro-1,3-benzenedicarboxylic acid (compound of Formula 13) oxidation products were separated as crude solids by filtration. The reaction conditions for Examples 1-9 are shown below in Table 1A, along with the total reaction times. The initial reaction mixture concentrations of the compound of Formula 1 were varied form about 5 to 50 wt % in the examples. The selectivity to the compound of Formula 2 was calculated by [(moles 3-methyl-2-nitrobenzoic acid (2) formed)/(moles 1,3-dimethyl-2-nitrobenzene (1) converted)]. Conversion and selectivities at specific times for Examples 1-9 are shown in Table 1B.

TABLE 1A

Material Loads and Rates of Addition for Examples 1 through 9

| Material | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| 1,3-dimethyl-2-nitrobenzene (1) (g) | 20 | 20 | 40 | 80 | 120 | 172 | 150 | 200 | 250 |
| Cobalt(II) acetate tetrahydrate (g) | 5 | 5 | 5 | 5 | 5 | 5 | 5 | 5 | 5 |
| Water (g) | 2 | 2 | 2 | 2 | 2 | 2 | 2 | 2 | 2 |
| Acetic acid (g) | 400 | 400 | 400 | 400 | 400 | 400 | 348 | 298 | 248 |
| Acetaldehyde Rate (mL/h) | 40 | 40 | 40 | 40 | 40 | 40 | 40 | 40 | 40 |
| Air Flow Rate (SLPM) | 2 | 2 | 2 | 2 | 2 | 2 | 2 | 2 | 2 |
| Run Time (h) | 4 | 6 | 4 | 4 | 2.7 | 2.7 | 4 | 4 | 4 |
| Initial wt % 1,3-dimethyl-2-nitrobenzene (1) in acetic acid | 4.8 | 4.8 | 9.1 | 16.7 | 23.1 | 30.1 | 30.1 | 40.2 | 50.2 |

TABLE 1B

Conversions and Selectivities at Specific Times for Examples 1-9

| | Ex. 1 | | | | Ex. 2 | | | | | | Ex. 3 | | | |
|---|---|---|---|---|---|---|---|---|---|---|---|---|---|---|
| | \multicolumn{14}{c}{Time (h)} |
| | 1 | 2 | 3 | 4 | 1 | 2 | 3 | 4 | 5 | 6 | 1 | 2 | 3 | 4 |
| Calc'd Conv. of (1) (%) | 80.8 | 96.4 | 98.9 | 99.5 | 87.3 | 96.8 | 98.9 | 99.6 | 99.6 | 99.7 | 60.2 | 80.9 | 92.9 | 96.3 |
| Calc'd Select. to (2) (%) | 74 | 44 | 28 | 22 | 71 | 45 | 31 | 22 | 19 | 15 | 79 | 68 | 59 | 51 |

TABLE 1B-continued

Conversions and Selectivities at Specific Times for Examples 1-9

| | Ex. | | | | | | | | | |
|---|---|---|---|---|---|---|---|---|---|---|
| | 4 | | | | 5 | | | 6 | | |
| | Time (h) | | | | | | | | | |
| | 1 | 2 | 3 | 4 | 1 | 2 | 2.7 | 1 | 2 | 2.7 |
| Calc'd Conv. of (1) (%) | 36.5 | 58.8 | 76.1 | 84.6 | 19.8 | 39.1 | 54.5 | 17.5 | 32.0 | 42.6 |
| Calc'd Select. to (2) (%) | 83 | 82 | 76 | 71 | 86 | 86 | 84 | 85 | 87 | 86 |

| | Ex. | | | | | | | | | | |
|---|---|---|---|---|---|---|---|---|---|---|---|
| | 7 | | | | 8 | | | | 9 | | |
| | Time (h) | | | | | | | | | | |
| | 1 | 2 | 3 | 4 | 1 | 2 | 3 | 4 | 1 | 2 | 3 | 4 |
| Calc'd Conv. of (1) (%) | 16.9 | 31.1 | 40.9 | 52.7 | 9.5 | 18.1 | 29.1 | 36.9 | 7.8 | 15.3 | 23.4 | 31.6 |
| Calc'd Select. to (2) (%) | 77 | 79 | 81 | 83 | 67 | 81 | 83 | 83 | 71 | 80 | 84 | 86 |

It was observed that the selectivity for 3-methyl-2-nitrobenzoic acid (the compound of Formula 2) was maximized above 70% between about 10 to 85% conversion of 1,3-dimethyl-2-nitrobenzene (1).

EXAMPLES 10 and 11

Synthesis of 3-methyl-2-nitrobenzoic acid (2)

Two oxidation experiments with 1,3-dimethyl-2-nitrobenzene (1) were completed in the pressure reactor under reaction conditions similar to those described for Examples 1-9. The specific conditions for each run are provided in Table 2A. In these runs, the reaction times were 5.5 h (Example 10) and 6.5 h (Example 11). Samples of the reaction mixture were collected immediately at the end of the oxidations and analyzed by GC. Table 2B provides the calculated 1,3-dimethyl-2-nitrobenzene (1) conversions and selectivities to 3-methyl-2-nitrobenzoic acid (2) for Examples 10 and 11 based on the GC analysis. In both cases, the 1,3-dimethyl-2-nitrobenzene (1) conversions exceeded 65%. Based on the conversion and selectivity for Example 10, the calculated mass of 3-methyl-2-nitrobenzoic acid (2) in the reaction mixture was about 103 g. Based on the conversion and selectivity for Example 11, the calculated mass of 3-methyl-2-nitrobenzoic acid (2) in the reaction mixture was about 110 g.

TABLE 2A

Material Loads and Rates of Addition for Examples 10 and 11

| | Ex. 10 | Ex. 11 |
|---|---|---|
| 1,3-dimethyl-2-nitrobenzene (1) (g) | 150 | 150 |
| Cobalt(II) acetate tetrahydrate (g) | 5 | 5 |
| Water (g) | 2 | 2 |
| Acetic acid (g) | 348 | 348 |
| Acetaldehyde Rate (mL/h) | 40 | 40 |
| Air Flow Rate (SLPM) | 2 | 2 |
| Run Time (h) | 5.5 | 6.5 |
| Reaction Temperature (° C.) | 100 | 100 |
| Agitator Speed (rpm) | 800 | 800 |
| Reactor pressure (N/m$^2$) | 3.45e+006 | 3.45e+006 |

TABLE 2B 1,3-Dimethyl-2-nitrobenzene (1) Conversions and 3-Methyl-2-nitrobenzoic acid (2) Selectivities for Examples 10 and 11, Based on GC analysis

| | Conv. of 1,3-dimethyl-2-nitrobenzene (1) (mole %) | Select. to 3-methyl-2-nitrobenzoic acid (2) (%) |
|---|---|---|
| Ex. 10 | 69.4 | 81.6 |
| Ex. 11 | 77.2 | 78.8 |

The oxidation product for Example 10 was collected and concentrated using a laboratory rotary evaporator apparatus at 70° C. and 30 mbar (3.0 kPa). After cooling to room temperature, the concentrate was slurried in 130 g of a 65 wt % acetic acid in water solution and then vacuum filtered using a coarse porosity glass Büchner filter funnel. The collected solid was then washed with a 65 wt % acetic acid in water solution (162 g), a 50 wt % acetic acid in water solution (155 g) and water (148 g). After air drying over several days, the mass of the dry solid was found to be 90.4 g. The crude solid had a composition of about 1% 1,3-dimethyl-2-nitrobenzene (1), 89.9% 3-methyl-2-nitrobenzoic acid (2) and 8.4% 2-nitro-1,3-benzenedicarboxylic acid (13) by GC analysis. The crude solid was combined with acetic acid (132.7 g), water (71.5 g) and sodium hydroxide (2.9 g) in a glass kettle. The mixture was heated to a gentle reflux (about 105° C.) for about 15 min during which time much of the solid dissolved. The mixture was then allowed to cool to room temperature. The solid that crystallized was isolated by vacuum filtration using a coarse porosity glass Büchner filter funnel. The solid was then washed with a 25 wt % acetic acid in water solution (80 g) and water (80 g). After air drying the mass of the dry solid was found to be 67.3 g. The recrystallized solid had a composition of about 0.13% 1,3-dimethyl-2-nitrobenzene (1), 99% 3-methyl-2-nitrobenzoic acid (2) and 0.72% 2-nitro-1,3-benzenedicarboxylic acid (13) by GC analysis. The calculated isolated mole yield of recrystallized 3-methyl-2-nitrobenzoic acid (2) was 37% for Example 10 based on the 1,3-dimethyl-2-nitrobenzene (1) loaded to the oxidation reactor.

The oxidation product for Example 11 was collected and concentrated using a laboratory rotary evaporator apparatus at 70° C. and 30 mbar (3.0 KpA) pressure. After cooling to room temperature, the concentrate was slurried in 124 g of a 25 wt % acetic acid in water solution and then vacuum filtered using a coarse porosity glass Büchner filter funnel. The product solid was then washed with a 25 wt % acetic acid in water solution (125 g) and three times with water (~122 g each time). The crude solid was then re-slurried in heptane (205 g) and again filtered and washed with heptane (68 g). After air drying over several days, the mass of the dry solid was found to be 107.6 g. The crude solid had a composition of about 1.2% 1,3-dimethyl-2-nitrobenzene (1), 79.2% 3-methyl-2-nitrobenzoic acid (2) and 17.3% 2-nitro-1,3-benzenedicarboxylic acid (13) by GC analysis. The crude solid was combined with acetic acid (159.4 g), water (85.6 g) and sodium hydroxide (6.69 g) in a glass kettle. The mixture was heated to a gentle reflux (about 105° C.) for about 15 min during which time much of the solid dissolved. The mixture was then allowed to cool to room temperature. The solid that crystallized was isolated by vacuum filtration using a coarse porosity glass Büchner filter funnel. The solid was then washed with a 25 wt % acetic acid in water solution (80 g) and four times with water (4×80 g). After air drying the mass of the dry solid was found to be 74.8 g. The recrystallized solid had a composition of about 0.1% 1,3-dimethyl-2-nitrobenzene (1), 98.4% 3-methyl-2-nitrobenzoic acid (2) and 1.2% 2-nitro-1,3-benzenedicarboxylic acid (13) by GC analysis. The calculated isolated mole yield of recrystallized 3-methyl-2-nitrobenzoic acid (2) was 41% for Example 11 based on the 1,3-dimethyl-2-nitrobenzene (1) loaded to the oxidation reactor.

EXAMPLE 12

Purification of 3-methyl-2-nitrobenzoic acid (2) by Recrystallization

Crude 3-methyl-2-nitrobenzoic acid (2) was recovered from several oxidation reactions and blended together. (The oxidations were completed at an average of <50% 1,3-dimethyl-2-nitrobenzene (1) conversion, as exemplified in Examples 5 through 9. The recovery was completed by allowing the reaction mixtures to cool to room temperature and then isolating the resulting solids by vacuum filtration using a 70-100 micron glass filter. The solids were then washed 3-4 times with acetic acid and/or acetic acid in water solutions (35-50 wt %) and with water before air drying and blending.) The blended crude 3-methyl-2-nitrobenzoic acid (2) (75.05 g) was slurried in a 35 wt % water in acetic acid solution (300 g). The mixture was then heated to reflux for about 30 min to dissolve most of the crude material. The mixture was cooled over 3 h to room temperature, after which time a precipitate formed. The precipitate was collected by filtration using a glass 25-50 micron glass filter under a mild vacuum. The solids were then washed with a 50 wt % water-acetic acid solution (100 mL) followed by water (100 mL). The product (64.59 g) was a crystalline, free flowing solid of 3-methyl-2-nitrobenzoic acid (2) with >99% purity by GC analysis. Crude and purified product analytical data for this process is provided below in Table 3.

TABLE 3

Recrystallization Example

| | Material Composition | | | | |
|---|---|---|---|---|---|
| | GC (Area %) | | | NAA (ppm) | Recovery |
| Material Identity | (1) | (2) | (13) | Cobalt | of (2) (%) |
| Crude 2 | 1.55 | 93.88 | 3.74 | ND | 91 |
| Recrystallized 2 | 0.00 | 99.14 | 0.86 | 11 | |

EXAMPLE 13

Purification of 3-methyl-2-nitrobenzoic acid (2) by Precipitation From Aqueous Base Crude 3-methyl-2-nitrobenzoic acid (2) was recovered from several oxidation reactions and blended together. (The oxidations were completed at an average of <50% 1,3-dimethyl-2-nitrobenzene (1) conversion, as exemplified in Examples 5 through 9. The recovery was completed by allowing the reaction mixtures to cool to room temperature and then isolating the resulting solids by vacuum filtration using a 70-100 micron glass filter. The solids were then washed 3-4 times with acetic acid and/or acetic acid in water solutions (35 to 50 wt %) and with water before air drying and blending.) The blended crude 3-methyl-2-nitrobenzoic acid (2) (20.16 g) was added to an aqueous sodium hydroxide solution (1 M, 144 mL) and stirred for 15 min to dissolve most of the crude material. An aqueous solution of hydrochloric acid was then added (3 M, 39 mL) slowly with stirring to reach a measured solution pH of 4.48. The precipitated solid was isolated by vacuum filtration using a 25-50 micron glass filter under mild vacuum and washed 2 times with water (100 mL). After air drying, the product (14.60 g) was an off-white solid of 3-methyl-2-nitrobenzoic acid (2) with 96.2% purity by GC analysis. Crude and purified product analytical data for this process is provided below in Table 4.

TABLE 4

Base-Acid Purification Example

| | Material Composition GC (Area %) | | | Recovery |
|---|---|---|---|---|
| Material Identity | (1) | (2) | (13) | of (2) (%) |
| Crude (2) | 1.83 | 93.70 | 3.86 | 74 |
| Precipitated (2) at pH 4.48 | 1.11 | 96.23 | 1.69 | |

EXAMPLE 14

Synthesis of 3-methyl-2-nitrobenzoic acid (2) (Run with 60% Loading of 1,3-dimethyl-2-nitrobenzene (1))

Three experiments on the air oxidations of 1,3-dimethyl-2-nitrobenzene (1) to 3-methyl-2-nitrobenzoic acid (2), Examples 14-1, 14-2 and 14-3, were carried out at a 60wt % initial loading of 1,3-dimethyl-2-nitrobenzene (1). The experiments were carried out in the pressure reactor applying operation procedures similar to those described for Examples 1 - 9. The specific conditions for each experiment are provided in Table 5.

TABLE 5

Material Loads and Rates of Addition for Examples 14-1, 14-2 and 14-3

| | 14-1 | 14-2 | 14-3 |
|---|---|---|---|
| Reactor Temperature (° C.) | 100 | 100 | 100 |
| 1,3-dimethyl-2-nitrobenzene (1) (g) | 300 | 300 | 300 |
| Cobalt(II) acetate tetrahydrate (g) | 5 | 5 | 5 |
| Water (g) | 2 | 2 | 2 |
| Acetic acid (g) | 198 | 198 | 198 |
| Acetaldehyde Rate (mL/h) | 40 | 40 | 40 |
| Air Flow Rate (slpm) | 2 | 2 | 2 |
| Agitator Speed (rpm) | 800 | 800 | 800 |
| Reactor pressure (psig) | 500 | 500 | 500 |
| Run Time (h) | 4 | 3.5 | 3.5 |

Process samples were collected every hour in Example 14-1. Only final reaction mixture samples were collected in Examples 14-2 and 14-3. These samples were analyzed by GC analysis and the reaction conversions and selectivities calculated. Table 6 provides the calculated 1,3-dimethyl-2-nitrobenzene (1) conversions and selectivities to 3-methyl-2-nitrobenzoic acid (2) for 14-1, 14-2 and 14-3 based on hourly and final samples taken during the oxidation experiments.

TABLE 6

Conversions and Selectivities at Specific Times for Examples 14-1, 14-2 and 14-3

| | 14-1 | | | | 14-2 | 14-3 |
|---|---|---|---|---|---|---|
| | Time (h) | | | | | |
| | 1 | 2 | 3 | 4 | 3.5 | 3.5 |
| Calc'd Conv. of (1) (%) | 10.0 | 18.8 | 25.3 | 33.0 | 27.0 | 28.1 |
| Calc'd Select. to (2) (%) | 75.1 | 84.5 | 86.2 | 86.6 | 87.0 | 87.2 |

TABLE 7

Material Loads and Rates of Addition for Examples 15-1, 15-2, 15-3 and 15-4

| | 15-1 | 15-4 | 15-2 | 15-3 |
|---|---|---|---|---|
| Reactor Temperature (° C.) | 90 | 100 | 110 | 115 |
| 1,3-dimethyl-2-nitrobenzene (1) (g) | 200 | 200 | 200 | 200 |
| Cobalt(II) acetate tetrahydrate (g) | 5 | 5 | 5 | 5 |
| Water (g) | 2 | 2 | 2 | 2 |
| Acetic acid (g) | 300 | 300 | 300 | 300 |
| Acetaldehyde Rate (mL/h) | 40 | 40 | 40 | 40 |
| Air Flow Rate (slpm) | 2 | 2 | 2 | 2 |
| Agitator Speed (rpm) | 800 | 800 | 800 | 800 |
| Reactor pressure (psig) | 500 | 500 | 500 | 500 |
| Run Time (h) | 4 | 4 | 4 | 4 |

TABLE 8

Conversions and Selectivities at Specific Times for Examples 15-1, 15-2, 15-3 and 15-4

| | 15-1 | | | | 15-4 | | | | 15-2 | | | | 15-3 | | | |
|---|---|---|---|---|---|---|---|---|---|---|---|---|---|---|---|---|
| | Time (h) | | | | | | | | | | | | | | | |
| | 1 | 2 | 3 | 4 | 1 | 2 | 3 | 4 | 1 | 2 | 3 | 4 | 1 | 2 | 3 | 4 |
| Calc'd Conv. of (1) (%) | 12 | 20 | 28 | 37 | 15 | 26 | 37 | 45 | 16 | 32 | 44 | 54 | 16 | 32 | 46 | 56 |
| Calc'd Select. to (2) (%) | 75 | 84 | 86 | 86 | 80 | 87 | 87 | 87 | 82 | 87 | 87 | 85 | 82 | 87 | 87 | 85 |

The data in Tables 5 and 6 demonstrates that the oxidation reaction can operate at an initial loading of 60wt % 1,3-dimethyl-2-nitrobenzene (1).

EXAMPLE 15

Synthesis of 3-methyl-2-nitrobenzoic acid (2)—Effects of Temperature

Four experiments on the air oxidations of 1,3-dimethyl-2-nitrobenzene (1) to 3-methyl-2-nitrobenzoic acid (2), Examples 15-1, 15-2, 15-3 and 15-4, were completed at four different reaction temperatures. The experiments were completed in the pressure reactor applying operation procedures similar to those described for Examples 1 - 9. The specific conditions for each experiment are provided in Table 7.

Process samples were collected every hour in Examples 15-1, 15-2, 15-3 and 15-4. These samples were analyzed by GC analysis and the reaction conversions and selectivities calculated. Table 8 provides the calculated 1,3-dimethyl-2-nitrobenzene (1) conversions and selectivities to 3-methyl-2-nitrobenzoic acid (2) for Examples 15-1, 15-2, 15-3 and 15-4 based on the hourly samples taken during the oxidation experiments.

The data in Tables 7 and 8 demonstrates that the oxidation reaction can provide high selectivities to 3-methyl-2-nitrobenzoic acid (2) between 90 and 115° C.

EXAMPLE 16

Synthesis of 3-methyl-2-nitrobenzoic acid (2)—Recycle Process Demonstration

Six experiments (examples 16A through 16F) were conducted in series to demonstrate the air oxidation of 1,3-dimethyl-2-nitrobenzene (1) to 3-methyl-2-nitrobenzoic acid (2) with recovery of crude 3-methyl-2-nitrobenzoic acid (2) and recycle of unreacted 1,3-dimethyl-2-nitrobenzene (1) and cobalt catalyst in a subsequent oxidation reaction. The targeted oxidation conditions used in examples 16A through 16F are outlined in Table 9.

TABLE 9

Targeted Oxidation Conditions for Examples 16A through 16F

| | |
|---|---|
| (1) Load (g) | 300 |
| Cobalt(II) Acetate · 4H$_2$O Load (g) | 6.25 |
| Acetic acid Load (g) | 300 |
| Acetaldehyde Feed Rate (mL/h) | 40 |
| Air Flow Rate (slpm) | 2 |
| Run Time (h) | 4 |
| Reaction Temperature (° C.) | 100 |
| Agitator Speed (rpm) | 800 |
| Reactor pressure (psig) | 500 |

The oxidation products were collected from the pressure reactor and concentrated using a laboratory rotary evaporator apparatus at 70° C., 30 mbar (3.0 kPa). A small amount of acetic acid (30-100 g) was added to the concentrated reaction mixture while it was still warm and then the mixture was allowed to cool to room temperature. After at least two hours at ambient temperature, the mixture was vacuum filtered using a coarse porosity glass Buchner filter. The resulting solid was washed with acetic acid twice (2×100 g). The crude 3-methyl-2-nitrobenzoic acid (2) was then washed once with water (1×100 g) and set aside to air dry. The crude solid was analyzed by GC to determine material composition.

The filtrate and acetic acid washes from the previous experiment were combined, weighed and analyzed by LC to quantitate the residual 1,3-dimethyl-2-nitrobenzene (1). Based on this analysis, a quantity of make-up 1,3-dimethyl-2-nitrobenzene (1) was then added to the filtrate and acetic acid washes to bring the total 1,3-dimethyl-2-nitrobenzene (1) to 300 grams. This was now the reformulated 1,3-dimethyl-2-nitrobenzene (1) feed for the next oxidation experiment. The required amount of make-up acetic acid to reformulate the reformulated 1,3-dimethyl-2-nitrobenzene (1) solution to a total target mass of 606.25 grams was then calculated and set aside. The reformulated 1,3-dimethyl-2-nitrobenzene (1) solution, make-up cobalt(II) acetate- $4H_2O$ catalyst and the make-up acetic acid were added to the oxidation reactor. The oxidation reaction, product recovery, and reformulation in preparation for subsequent experiments were then completed under the same conditions used in the first experiment.

Table 10 provides the actual raw material inputs and composition for the six oxidation experiments in examples 16A through 16F and Table 11 provides the mass and composition of the product streams during the recovery processes for examples 16A through 16F. The first experiment run is labelled A. Subsequent experiments are labelled B, C, D, E, F in order of experiments completed, respectively.

TABLE 10

| Actual Raw Material Inputs for Oxidation Examples 16A to 16F | | | | | | |
|---|---|---|---|---|---|---|
| Feed Materials | 16A | 16B | 16C | 16D | 16E | 16F |
| Amount of (1) charged (g) | 299.69 | 137.28 | 118.79 | 119.78 | 131.76 | 113.23 |
| Mass of reformulated feed (g) | — | 608.8 | 517.7 | 512.1 | 515.9 | 504.7 |
| Acetic acid charged (g) | 300.00 | 0.00 | 87.15 | 92.44 | 67.05 | 89.64 |
| Cobalt(II) acetate tetrahydrate added (g) | 6.2515 | 0.5082 | 0.4905 | 0.4933 | 0.4961 | 2.6801 |

TABLE 11

| Mass and Composition of the Product Streams During Recovery Processes for Examples 16A to 16F | | | | | | |
|---|---|---|---|---|---|---|
| Products | 16A | 16B | 16C | 16D | 16E | 16F |
| Reaction mixture mass exiting reactor (g) | 779.73 | 781.57 | 768.98 | 771.53 | 771.08 | 776.22 |
| Concentrated reaction mixture mass (g) | 319.99 | 359.90 | 358.60 | 356.14 | 369.98 | 363.61 |
| Filtrate + acetic acid rinses of solid (g) | 472.39 | 400.18 | 393.52 | 408.32 | 403.67 | 384.43 |
| Crude (2) solids, dry (g) | 97.19 | 118.41 | 112.95 | 103.76 | 105.03 | 108.06 |
| Purity of crude (2) (GC Area %) | 88.69 | 89.78 | 87.04 | 91.04 | 89.37 | 88.67 |
| Amount of (2) in crude (g) | 86.20 | 106.31 | 98.31 | 94.46 | 93.87 | 95.82 |

Table 12 provides the cumulative yields of pure product in the crude 3-methyl-2-nitrobenzoic acid (2) based on the 1,3-dimethyl-2-nitrobenzene (1) added to the process. Ignoring the initial 1,3-dimethyl-2-nitrobenzene (1) loading (experiment A), the data for examples 16A through 16F shows that the cumulative yield stays constant at about 64-68% across experiments B to F.

TABLE 12

| Cumulative Yields for Examples 16A to 16F | | | | | | |
|---|---|---|---|---|---|---|
| Yield | 16A | 16B | 16C | 16D | 16E | 16F |
| Cumulative yield of (2) in crude based on (1) added (%) | 24.0 | 36.8 | 43.5 | 47.5 | 50.6 | 53.1 |
| Cumulative yield of (2) in crude based on (1) added, excluding 16A (%) | — | 64.6 | 66.4 | 66.2 | 66.9 | 67.6 |

The cumulative yield of 3-methyl-2-nitrobenzoic acid (2) in the crude solid for examples 16 were calculated in the following way:

Cumulative Yield (2) in crude solid from experiment A to experiment X=[(total moles 3-methyl-2-nitrobenzoic acid (2) isolated in experiment A through X)/(moles 1,3-dimethyl-2-nitrobenzene (1) loaded in experiment A through X)]×100. Experiment X is either experiment B, C, D, E or F.

Cumulative Yield (2) in crude solid from experiment B to experiment X =[(total moles 3-methyl-2-nitrobenzoic acid (2) isolated in experiment B through X)/(moles 1,3-dimethyl-2-nitrobenzene (1) loaded in experiment B through X)]×100. Experiment X is either experiment C, D, E or F.

EXAMPLE 17

Synthesis of 3-methyl-2-nitrobenzoic acid (2)—Recycle Process Demonstration

A multi-experiment study was completed, involving ten experiments (examples 17A through 17J), to demonstrate the air oxidation of 1,3-dimethyl-2-nitrobenzene (1) to 3-methyl-2-nitrobenzoic acid (2) with recovery of crude 3-methyl-2-nitrobenzoic acid (2) and recycle of unreacted 1,3-dimethyl-2-nitrobenzene (1) and cobalt catalyst in a subsequent oxidation reaction. The targeted oxidation conditions used in examples 17A through 17J are outlined in Table 13.

TABLE 13

| Targeted Oxidation Conditions for Examples 17A through 17J | |
|---|---|
| (1) Load (g) | 400 |
| Cobalt(II) Acetate · 4H$_2$O Load (g) | 7.5 |
| Acetic acid Load (g) | 200 |
| Acetaldehyde Feed Rate (mL/h) | 40 |
| Air Flow Rate (slpm) | 2.0 |
| Run Time (h) | 4.0* |
| Reaction Temperature (° C.) | 100 |
| Agitator Speed (rpm) | 1600 |
| Reactor pressure (psig) | 500 |

*Experiment 1C and 1F were terminated at 3.7 and 2.9 hours respectively

The oxidation reactions were completed as described in prior examples. At the end of the oxidation, the reactor pressure and agitator speed were reduced to 50 psig and 400 rpm and the reaction products were cooled from reaction temperature to 35° C. The oxidation products were then discharge and collected from the pressure reactor and the reactor was rinsed with acetic acid (~100 g). The oxidation products were placed in an ice bath to cool for at least one hour and then the cold mixture was vacuum filtered using a coarse porosity glass Buchner filter. The recovered solid was washed with the reactor rinse acetic acid and acetic acid (~100 g). The crude 3-methyl-2-nitrobenzoic acid (2) was set aside to air dry. The crude solid was analyzed by LC to determine material composition.

The filtrate and acetic acid washes were combined and weighed. A calculated mass of acetic acid and water were then removed by distillation at elevated temperature (50-80° C.) and reduced pressure (50-60 torr) to bring the mass of the concentrate to approximately 465 grams. 1,3-dimethyl-2-nitrobenzene (1) (typically ~128 g) was added to the concentrate to give the reformulated 1,3-dimethyl-2-nitrobenzene (1) feed for the next oxidation experiment. The required amount of make-up acetic acid to bring the reformulated 1,3-dimethyl-2-nitrobenzene (1) solution to a total target mass of approximately 606 grams was then calculated. The reformulated 1,3-dimethyl-2-nitrobenzene (1) solution and make-up acetic acid were then added to the oxidation reactor for the next experiment of the multi-experiment process.

In experiment 17C, an equipment issue led to the termination of the oxidation process at 3.7 hours. In experiment 17F, an equipment issue led to the termination of the oxidation process at 2.9 hours. Consequently, only 100 grams of make-up 1,3-dimethyl-2-nitrobenzene (1) was added in experiment 17G. With the exception of these minor changes to the oxidation reaction time and make-up 1,3-dimethyl-2-nitrobenzene (1) added, the same conditions were applied for the oxidation reaction, product recovery and reformulation processes in all experiments.

Table 14 provides the actual raw material inputs and composition for the ten oxidation experiments in examples 17A through 17J. Table 15 provides the mass and composition of the product streams during the recovery processes for examples 1A through 1J. The first experiment run is labelled A. Subsequent experiments are labelled B, C, D, E, F, G, H, I and J in order of experiments completed, respectively. No additional cobalt catalyst was added in experiments B through J.

TABLE 14

| Actual Raw Material Inputs for Oxidation Examples 1A to 1J | | | | | | | | | | |
|---|---|---|---|---|---|---|---|---|---|---|
| Feed Materials | 17A | 17B | 17C | 17D | 17E | 17F | 17G | 17H | 17I | 17J |
| (1) charged (g) | 399.94 | 127.81 | 127.97 | 127.98 | 128.00 | 128.00 | 100.0 | 128.08 | 128.00 | 127.98 |
| Mass of reformulated feed (g) | — | 583.36 | 595.26 | 594.62 | 594.47 | 592.11 | 592.12 | 578.95 | 598.13 | 596.35 |
| Acetic acid charged (g) | 200.32 | 23.55 | 11.15 | 11.13 | 10.99 | 14.02 | 13.01 | 26.58 | 7.56 | 10.77 |
| Fresh Cobalt(II) acetate tetrahydrate charged (g) | 7.51 | 0 | 0 | 0 | 0 | 0 | 0 | 0 | 0 | 0 |

TABLE 15

Mass and Composition of the Product Streams During Recovery Processes for Examples 17A to 17J

| Feed Materials | 17A | 17B | 17C | 17D | 71E | 17F | 17G | 17H | 17I | 17J |
|---|---|---|---|---|---|---|---|---|---|---|
| Reaction mixture mass exiting reactor (g) | 775.52 | 766.41 | 759.21 | 757.60 | 768.00 | 713.04 | 770.29 | 763.19 | 763.10 | 767.95 |
| Crude (2) solids recovered, dry (g) | 95.15 | 123.14 | 126.83 | 120.2 | 118.47 | 102.61 | 122.46 | 123.88 | 117.92 | 118.13 |
| Filtrate and acetic acid rinses (g) | 826.14 | 770.76 | 729.45 | 734.90 | 754.98 | 727.75 | 729.03 | 701.57 | 725.67 | 744.66 |
| Concentrated reaction mixture mass (g) | 457.34 | 469.96 | 467.05 | 467.28 | 462.08 | 464.14 | 453.93 | 471.04 | 468.37 | — |
| Purity of crude solid (2) (LC) | 94.2 | 92.5 | 86.6 | 94.0 | 89.1 | 80.8 | 87.8 | 86.3 | 90.4 | 85.2 |
| (2) contained in crude (g) | 89.63 | 113.90 | 109.83 | 112.99 | 105.56 | 82.92 | 107.48 | 106.91 | 106.60 | 100.65 |

Table 16 provides the cumulative yields of pure product in the crude 3-methyl-2-nitrobenzoic acid (2) based on the 1,3-dimethyl-2-nitrobenzene (1) added to the process. Ignoring the initial 1,3-dimethyl-2-nitrobenzene (1) loading (experiment A), the data for examples 17A through 17J shows that the cumulative yield stays constant at about 69-74% across experiments B to J.

TABLE 16

Cumulative Yields for Examples 17A to 17J

| Yield | 17A | 17B | 17C | 17D | 71E | 17F | 17G | 17H | 17I | 17J |
|---|---|---|---|---|---|---|---|---|---|---|
| Cumulative yield of (2) in crude based on (1) added (%) | 18.7 | 32.2 | 39.9 | 45.4 | 48.7 | 49.3 | 52.9 | 54.6 | 55.9 | 56.8 |
| Cumulative yield of (2) in crude based on (1) added, excluding 1A (%) | — | 74.4 | 73.0 | 73.2 | 72.1 | 68.5 | 71.4 | 71.1 | 70.9 | 70.3 |

The cumulative yield of 3-methyl-2-nitrobenzoic acid (2) in the crude solid were calculated in the following way:

Cumulative Yield (2) in crude solid from experiment A to experiment X =[(total moles 3-methyl-2-nitrobenzoic acid (2) isolated in experiment A through X)/(moles 1,3-dimethyl-2-nitrobenzene (1) loaded in experiment A through X)]×100. Experiment X is either experiment B, C, D, E, F, G, H, I or J.

Cumulative Yield (2) in crude solid from experiment B to experiment X =[(total moles 3-methyl-2-nitrobenzoic acid (2) isolated in experiment B through X)/(moles 1,3-dimethyl-2-nitrobenzene (1) loaded in experiment B through X)]×100. Experiment X is either experiment C, D, E, F, G, H, I or J.

EXAMPLE 18

Synthesis of 3-methyl-2-nitrobenzoic acid (2)—Absence of Catalyst

Two experiments on the air oxidations of 1,3-dimethyl-2-nitrobenzene (1) to 3-methyl-2-nitrobenzoic acid (2), Examples 18-1 and 18-2, were completed with no cobalt catalyst added. The experiments were completed in the pressure reactor applying operation procedures similar to those described for Examples 1 - 9. The specific conditions for each experiment are provided in Table 17.

Prior to Example 18-1 the oxidation reactor was cleaned using methanol to remove trace Co catalyst from prior experiments. Based on the unexpected result for Example 18-1, Example 18-2 was completed. Prior to Example 18-2 the oxidation reactor was carefully cleaned using methanol (1×600 g) at 50 ° C. and with acetic acid (2×600 g) at 100° C. to remove trace Co catalyst from prior experiments Process samples were collected at the termination of the run for Examples 18-1 and 18-2. These samples were analyzed by LC analysis and the reaction conversions and yields calculated. Table 18 provides the calculated 1,3-dimethyl-2-nitrobenzene (1) conversions and yields of 3-methyl-2-nitrobenzoic acid (2) for Examples 18-2 and 18-2 based on the samples taken at the termination of the oxidation experiments.

The data in Tables 17 and 18 demonstrates that the oxidation reaction can provide 3-methyl-2-nitrobenzoic acid (2) when no catalyst is present.

TABLE 17

Material Loads and Rates of Addition for Examples 18-1 and 18-2

| | 18-1 | 18-2 |
|---|---|---|
| Reactor Temperature (° C.) | 100 | 100 |
| 1,3-dimethyl-2-nitrobenzene (1) (g) | 400 | 400 |
| Cobalt(II) acetate tetrahydrate (g) | 0 | 0 |
| Acetic acid (g) | 200 | 200 |
| Acetaldehyde Rate (mL/h) | 40 | 40 |
| Air Flow Rate (slpm) | 2 | 2 |
| Agitator Speed (rpm) | 1600 | 1600 |
| Reactor pressure (psig) | 500 | 500 |
| Run Time (h) | 2.3 | 4 |

TABLE 18

Conversions and Yields at Specific Times for Examples 18-1 and 18-2

| | 1-1 | 1-2 |
|---|---|---|
| Time (h) | 2.3 | 4 |
| Calc'd Conv. of (1) (%) | 13.8 | 23.0 |
| Calc'd Select. to (2) (%) | 35.0 | 37.9 |

The conversion of 1,3-dimethyl-2-nitrobenzene (1) and the yield of 3-methyl-2-nitrobenzoic acid (2) in the reaction mixture were calculated in the following way: Calc'd Conv. of (1) in reaction mixture=[{(moles 1,3-dimethyl-2-nitrobenzene (1) loaded)−((moles 1,3-dimethyl-2-nitrobenzene (1) remaining in reaction mixture measured by LC)}/(moles 1, 3-dimethyl-2-nitrobenzene (1) loaded)]×100

Calc'd Select. to (2) in reaction mixture =[(moles 3-methyl-2-nitrobenzoic acid (2) in reaction mixture measured by LC)/{(moles 1,3-dimethyl-2-nitrobenzene (1) loaded)−((moles 1,3-dimethyl-2-nitrobenzene (1) remaining in reaction mixture measured by LC}]×100.

The invention claimed is:

1. A method for preparing a compound of Formula 7

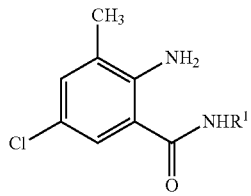

7 wherein $R^1$ is $C_1$-$C_7$ alkyl, $C_3$-$C_6$ cycloalkyl or $C_4$-$C_7$ alkylcycloalkyl;
comprising (A) contacting a compound of Formula 2

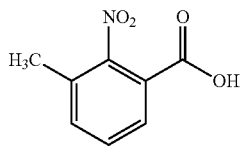

2 with a reducing agent to form a compound of Formula 3

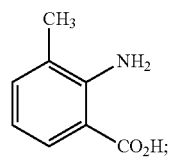

3

(B) contacting the compound of Formula 3
with $R^2OC(=O)Cl$ to form a compound of Formula 4

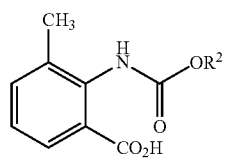

4 wherein $R^2$ is $C_1$-$C_6$ alkyl or $C_3$-$C_6$ alkenyl, each optionally substituted with up to 3 halogen and up to 1 phenyl;
(C) contacting the compound of Formula 4
with a chlorinating agent to form a compound of Formula 5

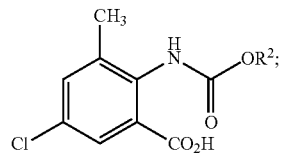

5

(D) contacting the compound of Formula 5
with a cyclizing agent to form a compound of Formula 6

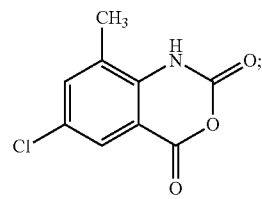

6

(E) contacting the compound of Formula 6
with $R^1NH_2$ to form the compound of Formula 7;
characterized by using the compound of Formula 2 as prepared by a method comprising, contacting a compound of Formula 1

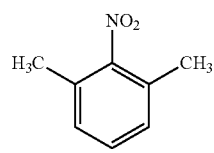

1 with an oxidation catalyst in the presence of an oxygen source and an initiator, provided that less than 99% of a compound of Formula 1 is oxidized.

2. The method of claim 1 wherein $R^1$ is $C_1$-$C_4$ alkyl or $C_3$-$C_6$ cycloalkyl.

3. The method of claim 2 wherein $R^1$ is methyl, isopropyl, cyclopropyl or t-butyl.

4. The method of claim 3 wherein $R^1$ is methyl or t-butyl.

5. The method of claim 1 wherein $R^2$ is $C_1$-$C_4$ alkyl.

6. The method of claim 5 wherein $R^2$ is methyl or ethyl.

7. The method of claim 6 wherein $R^2$ is ethyl.

8. The method of claim 1 wherein the cyclizing agent is $PBr_3$.

9. The method of claim 1 wherein the chlorinating agent is HCl and $H_2O_2$.

10. A method for preparing a compound of Formula 11

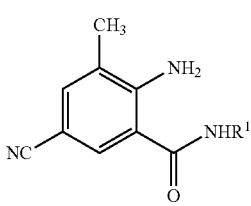

11 wherein $R^1$ is $C_1$-$C_7$ alkyl, $C_3$-$C_6$ cycloalkyl or $C_4$-$C_7$ alkylcycloalkyl;
comprising (A) contacting a compound of Formula 2

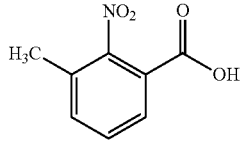
2 with an activating agent and $R^1NH_2$ to form a compound of Formula 8;

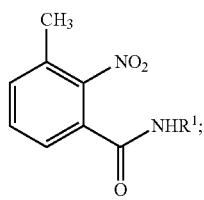
8

(B) contacting the compound of Formula 8
with a reducing agent to form a compound of Formula 9

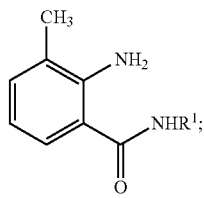
9

(C) contacting the compound of Formula 9
with a brominating agent to form a compound of Formula 10

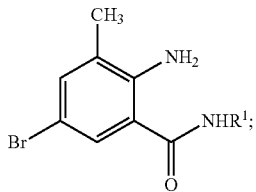
10

(D) contacting the compound of Formula 10
with a cyanating agent to form the compound of Formula 11;
characterized by using the compound of Formula 2 as prepared by a method comprising, contacting a compound of Formula 1

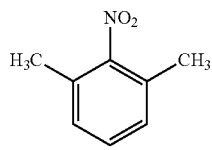
1 with an oxidation catalyst in the presence of an oxygen source and an initiator, provided that less than 99% of a compound of Formula 1 is oxidized.

11. The method of claim 10 wherein $R^1$ is $C_1$-$C_4$ alkyl or $C_3$-$C_6$ cycloalkyl.

12. The method of claim 11 wherein $R^1$ is methyl, isopropyl, cyclopropyl or t-butyl.

13. The method of claim 12 wherein $R^1$ is methyl or t-butyl.

14. The method of claim 13 wherein $R^1$ is methyl.

15. The method of claim 14 wherein $R^1$ is t-butyl.

* * * * *